US007465580B2

(12) United States Patent
Sugden et al.

(10) Patent No.: US 7,465,580 B2
(45) Date of Patent: Dec. 16, 2008

(54) NON-CYTOTOXIC ORIP REPLICON

(75) Inventors: William M. Sugden, Madison, WI (US); Jindong Wang, Madison, WI (US); Gregory Dean Kennedy, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 386 days.

(21) Appl. No.: 10/848,976

(22) Filed: May 19, 2004

(65) Prior Publication Data

US 2005/0260564 A1 Nov. 24, 2005

(51) Int. Cl.
 *C12N 15/00* (2006.01)
 *C12N 7/08* (2006.01)
 *C12N 5/06* (2006.01)
 *A61K 39/395* (2006.01)
 *A61K 39/245* (2006.01)
(52) U.S. Cl. ............... 435/320.1; 435/237; 435/326; 424/152.1; 424/230.1
(58) Field of Classification Search ............... None
 See application file for complete search history.

(56) References Cited

U.S. PATENT DOCUMENTS

| 4,686,186 | A | 8/1987 | Sugden |
| 5,194,601 | A | 3/1993 | Sugden |
| 5,707,830 | A | 1/1998 | Calos |
| 2002/0068354 | A1 | 6/2002 | Johnson et al. |
| 2003/0099936 | A1 | 5/2003 | Sugden et al. |
| 2003/0109475 | A1 | 6/2003 | Debs et al. |

FOREIGN PATENT DOCUMENTS

WO WO 00/47778 * 8/2000

OTHER PUBLICATIONS

Hung et al., Maintenance of EBV oriP-based spisomes requires EBV-encoded nuclear antiten-1 chromosome-binding domains, which can be replaced by high-mobility group-I or histone H1, Proceedings of the National Academy of Sciences of the United States of America (PNAS), Feb. 2001, vol. 98, No. 4, pp. 1865-1870.*
Aiyar, A., et al., "The Plasmid Replicon of EBV Consists of Multiple cis-Acting Elements that Facilitate DNA Synthesis by the Cell and a Viral Maintenance Element", *The EMBO Journal*, 17(21), (1998),6394-6403.
Arrand, J R., et al., "Molecular cloning of the Complete Epstein-Barr Virus Genome as a Set of Overlapping Restriction Endonuclease Fragments", *Nucleic Acids Research*, 9(13), (Jul. 10, 1981),2999-3014.
Baer, R J., et al., "DNA Sequence and Expression of the B95-8 Epstein-Barr Virus Genome", *Nature*, 310(5974), (1984),207-211.
Bankier, A T., et al., "DNA Sequence Analysis of the EcoRI Dhet Fragment of B95-8 Epstein-Barr Virus Containing the Terminal Repeat Sequences", *Molecular Biology and Medicine*, 1(4), (1983),425-445.

Bankier, A T., et al., "Sequence Analysis of the 17,166 Base-Pair EcoRI Fragment C of B95-8 Epstein-Barr Virus", *Molecular Biology and Medicine*, 1(1), (Jul. 1983),21-45.
Biggin, M , et al., "Transcription and DNA Sequence of the BamHI L Fragment of B95-8 Epstein-Barr Virus", *The EMBO Journal*, 3(5), (May 1984), 1083-1090.
Deininger, P L., et al., "Sequence Analysis and in Vitro Transcription of Portions of the Epstein-Barr Virus Genome", *Journal of Cellular Biochemistry*, 19(3), (1982),267-74.
Farrell, P J., et al., "Homologous Upstream Sequences Near Epstein-Barr Virus Promoters", *Proc. Natl. Acad. Sci. USA.*, 80(6), (1983),1565-1569.
Farrell, P J., et al., "Latent and Lytic Cycle Promoters of Epstein-Barr Virus", *The EMBO Journal*, 2(8), (1983), 1331-1338.
Gibson, T., et al., "Homology Between Two EBV Early Genes and HSV Ribonucleotide Reductase and 38K Genes", *Nucleic Acids Research*, 12(12), (1984),5087-5099.
Holowaty, M. N., et al., "Protein Profiling With Epstein-Barr Nuclear Antigen-1 Reveals an Interaction With the Herpesvirus-Associated Ubiquitin-Specific Protease HAUSP/USP7", *The Journal of Biological Chemistry*, 278(32), (2003),29987-29994.
Huang, N E., et al., "Modulation of YY1 Activity by SAP30", *Biochemical and Biophysical Research Communications.*, vol. 306(1), (2003),267-275.
Humme, S., et al., "The EBV Nuclear Antigen 1 (EBNA1) Enhances B Cell Immortalization Several Thousandfold", *Proc. Natl. Acad. Sci. USA*, 100(19), (2003), 10989-10994.
Jeang, K T., et al., "Organization of the Epstein-Barr Virus DNA Molecule. III. Location of the P3HR-1 Deletion Junction and Characterization of the NotI Repeat Units that Form Part of the Template for an Abundant 12-O-Tetradecanoylphorbol-13-Acetate-Induced mRNA Transcript", *Journal of Virology*, 48(1), (1983),135-148.
Jones, R. J., et al., "Epstein-Barr Virus Nuclear Antigen 1 (EBNA1) Induced Cytotoxicity in Epithelial Cells is Associated With EBNA1 Degradation and Processing", *Virology*, 313, (2003),663-676.
Jones, M D., et al., "The EB Virus Genome in Daudi Burkitt's Lymphoma Cells has a Deletion Similar to that Observed in a Non-Transforming Strain (P3HR-1) of the Virus", *The EMBO Journal*, 3(4), (1984),813-821.
Kaneda, Y., "Improvements in Gene Therapy Technologies", *Molecular Urology*, 5(2), (2001),85-89.
Kang, M.-S., et al., "Epstein-Barr Virus Nuclear Antigen 1 Activates Transcription From Episomal But Not Integrated DNA and Does Not Alter Lymphocyte Growth", *Proc. Natl. Acad. of Sci. USA*, 98(26), (2001),15233-15238.
Kennedy, G., et al., "Chapter 3.2 Virus-Based Vectors for Gene Expression in Mammalian Cells: Epstein-Barr Virus", *In: Gene Transfer and Expression in Mammalian Cells*, S. C. Makrides, Editor, Elsevier Science B.V., Publisher,(2003),55-70.

(Continued)

*Primary Examiner*—Bruce Campell
*Assistant Examiner*—Sharon Hurt
(74) *Attorney, Agent, or Firm*—Schwegman, Lundberg & Woessner, P.A.

(57) ABSTRACT

The invention provides a vector encoding a derivative of EBNA-1 that is not cytotoxic when expressed efficiently in cells, which supports extrachromosomal replication, maintenance and transcription from extrachromosomal oriP containing vectors but does not substantially activate transcription from host cell genes. Also provided is a vector having oriP and encoding a derivative of EBNA-1. The vectors of the invention may be employed in vitro and in gene therapy.

36 Claims, 15 Drawing Sheets

OTHER PUBLICATIONS

Kennedy, G., et al., "EBNA-1, a Bifunctional Transcriptional Activator", *Molecular Cellular Biology*, 23(19), (2003),6901-6908.

Kennedy, G., et al., "Epstein-Barr Virus Provides a Survival Factor to Burkitt's Lymphomas", *Proc. Natl. Acad. Sci. USA.*, 100(24), (2003), 14269-14274.

Kozak, M., "Possible Role of Flanking Nucleotides in Recognition of the AUG Initiator Codon by Eukaryotic Ribosomes", *Nucleic Acids Research*, 9(20), (1981),5233-52.

Kurisaki, K., et al., "Nuclear Factor YY1 Inhibits Transforming Growth Factor beta- and Bone Morphogenetic Protein-Induced Cell Differentiation", *Molecular and Cellular Biology.*, vol. 23(13), (2003),4494-4510.

Laux, G., et al., "A Spliced Epstein-Barr Virus Gene Expressed in Immortalized Lymphocytes is Created by Circularization of the Linear Viral Genome", *The EMBO Journal*, 7(3), (1988),769-774.

Leight, E. R., et al., "EBNA-1: A Protein Pivotal to Laten Infection by Epstein-Barr Virus", *Reviews in Medical Virology*, 10, (2000),83-100.

Levitskaya, J., et al., "Inhibition of Antigen Processing by the Internal Repeat Region of the Epstein-Barr Virus Nuclear Antigen-1", *Nature*, 375, (1995),685-688.

Mazda, O., "Improvement of Nonviral Gene Therapy by Epstein-Barr Virus (EBV)-based Plasmid Vectors", *Current Gene Therapy*, 2(3), (2002),379-392.

Parker, B D., et al., "Sequence and Transcription of Raji Epstein-Barr Virus DNA Spanning the B95-8 Deletion Region", *Virology*, 179(1), (1990),339-346.

Séguin, C., et al., "DNA Sequence and Transcription of the *Bam*HI Fragment B Region of B95-8 Epstein-Barr virus", *Mol Biol Med.*, 1(3), (1983),369-392.

Shire, K., et al., "EBP2, a Human Protein That Interacts With Sequences of the Epstein-Barr Virus Nuclear Antigen 1 Important for Plasmid Maintenance", *Journal of Virology*, 73(4), (1999),2587-2595.

Sucharov, C C., et al., "Yin Yang 1 is Increased in Human Heart Failure and Represses the Activity of the Human α-Myosin Heavy Chain Promoter", *The Journal of Biological Chemistry*, vol. 278(33), (2003),31233-31239.

Sugden, B., et al., "EBV's Plasmid Replicon: an Enigma in *cis* and *trans*", *Current Topics in Microbiology and Immunology*, 258, (2001),3-11.

Sugden, B., "In the Beginning: A Viral Origin Exploits the Cell", *Trends in Biochemical Sciences*, 27(1), (2002),1-3.

Wu, H., et al., "Separation of the DNA Replication, Segregation, and Transcriptional Activation Functions of Epstein-Barr Nuclear Antigen 1", *Journal of Virology*, 76(5), (2002),2480-2490.

Yates, J., et al., "A *cis*-Acting Element from the Epstein-Barr Viral Genome that Permits Stable Replication of Recombinant Plasmids in Latently Infected Cells", *Proc. Natl. Acad. Sci. USA.*, 81(12), (Jun. 1984),3806-3810.

Yin, Y., et al., "Self-Inhibition of Synthesis and Antigen Presentation by Epstein-Barr Virus-Encoded EBNA1", *Science*, 301, (2003),1371-1374.

Bodescot, M., et al., "Clustered Alternative Splice Sites in Epstein-Barr Virus RNAs", *Nucleic Acids Research*, 15(14), (1987),5887.

* cited by examiner

|0.4|1.2|6.3|0.6|4.5|2.1|3.3|
Relative Expression levels
of the EBNA-1 derivatives

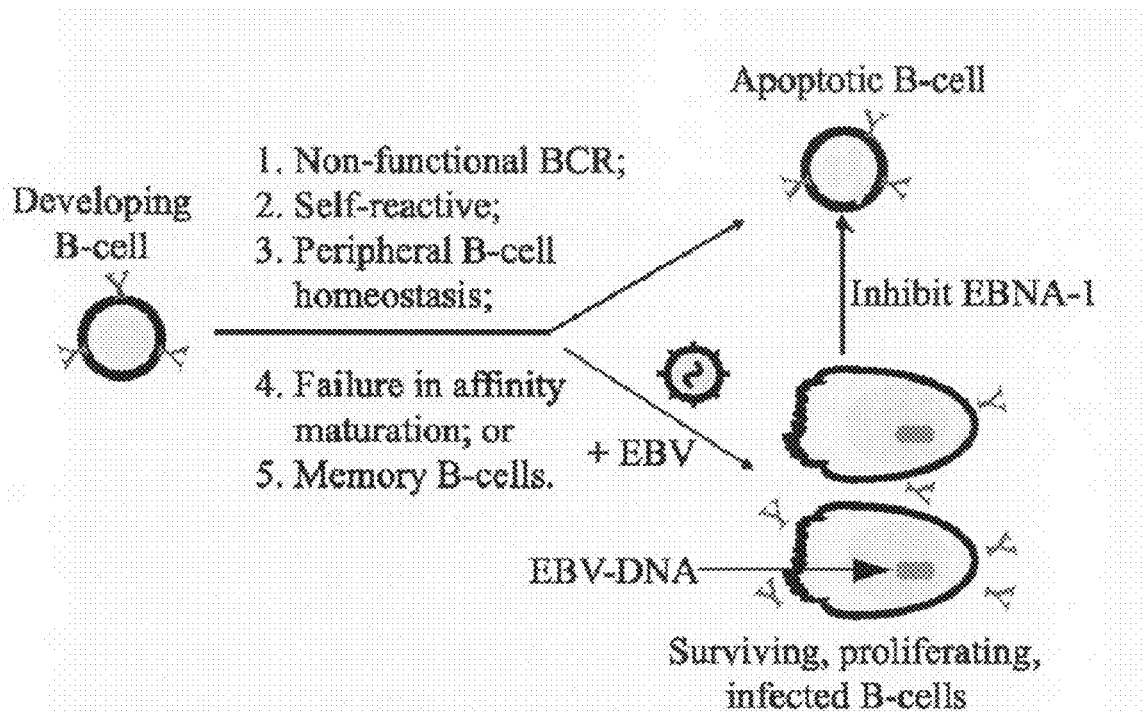

FIG. 11

```
  1 msdegpgtgp gnglgekgdt sgpegsggsg pqrrggdnhg rgrgrgrgrg ggrpgapggs
 61 gsgprhrdgv rrpqkrpsci gckgthggtg agagaggaga ggagagggag agggaggagg
121 aggagaggga gagggaggag gagagggaga gggaggagag ggaggaggag agggagaggg
181 aggagaggga ggaggagagg gagaggagga ggagagggaga gggaggagga gaggagagga
241 gaggagagga ggagaggagg agaggaggag agggaggaga gggaggagag gaggagagga
301 ggagaggagg agaggggagag gagaggggrg rggsggrgrg gsggrgrggs ggrrgrgrer
361 arggsrerar grgrgrgekr prspssqsss sgspprrppp grrpffhpvg eadyfeyhqe
421 ggpdgepdvp pgaieqgpad dpgegpstgp rgqgdggrrk kggwfgkhrg qggsnpkfen
481 iaeglralla rshverttde gtwvagvfvy ggsktslynl rrgtalaipq crltplsrlp
541 fgmapgpgpq pgplresivc yfmvflqthi faevlkdaik dlvmtkpapt cnlrvtvcsf
601 ddgvdlppwf ppmvegaaae gddgddgdeg gdgdegeegq e
```

FIG. 12

SEQUENCE LISTING

<160> NUMBER OF SEQ ID NOS: 18

<210> SEQ ID NO 1
<211> LENGTH: 641
<212> TYPE: PRT
<213> ORGANISM: Epstein-Barr virus

<400> SEQUENCE: 1

```
Met Ser Asp Glu Gly Pro Gly Thr Gly Pro Gly Asn Gly Leu Gly Glu
 1               5                  10                  15

Lys Gly Asp Thr Ser Gly Pro Glu Gly Ser Gly Gly Ser Gly Pro Gln
             20                  25                  30

Arg Arg Gly Gly Asp Asn His Gly Arg Gly Arg Gly Arg Gly Arg Gly
         35                  40                  45

Arg Gly Gly Gly Arg Pro Gly Ala Pro Gly Gly Ser Gly Ser Gly Pro
     50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                 85                  90                  95

Gly Ala Gly Ala Gly Gly Ala Gly Ala Gly Gly Ala Gly Ala Gly Gly
            100                 105                 110

Gly Gly Ala Gly Gly Ala Gly Gly Ala Gly Gly Ala Gly Ala Gly Gly
        115                 120                 125

Gly Ala Gly Ala Gly Gly Ala Gly Gly Ala Gly Gly Ala Gly Ala Gly
    130                 135                 140

Gly Gly Ala Gly Ala Gly Gly Ala Gly Gly Ala Gly Ala Gly Gly Ala Gly
145                 150                 155                 160

Gly Gly Ala Gly Gly Ala Gly Gly Ala Gly Ala Gly Gly Gly Ala Gly
                165                 170                 175

Ala Gly Gly Gly Ala Gly Gly Ala Gly Ala Gly Gly Gly Ala Gly Gly
            180                 185                 190

Ala Gly Gly Ala Gly Ala Gly Gly Gly Ala Gly Ala Gly Gly Ala Gly
        195                 200                 205

Gly Ala Gly Gly Ala Gly Ala Gly Gly Ala Gly Ala Gly Gly Gly Ala
    210                 215                 220

Gly Gly Ala Gly Gly Ala Gly Ala Gly Ala Gly Gly Ala Gly Gly Ala
225                 230                 235                 240

Gly Ala Gly Gly Ala Gly Ala Gly Gly Ala Gly Gly Ala Gly Ala Gly
                245                 250                 255

Gly Ala Gly Gly Ala Gly Ala Gly Gly Ala Gly Gly Ala Gly Ala Gly
            260                 265                 270

Gly Gly Ala Gly Gly Ala Gly Ala Gly Gly Ala Gly Gly Ala Gly Ala Gly
        275                 280                 285

Ala Gly Gly Ala Gly Gly Ala Gly Ala Gly Gly Ala Gly Gly Ala Gly
    290                 295                 300

Ala Gly Gly Ala Gly Ala Gly Ala Gly Gly Ala Gly Gly Ala Gly Ala Gly
305                 310                 315                 320

Gly Ala Gly Ala Gly Gly Gly Gly Arg Gly Arg Gly Gly Ser Gly Gly
                325                 330                 335

Arg Gly Arg Gly Gly Ser Gly Gly Arg Gly Arg Gly Gly Ser Gly Gly
            340                 345                 350

Arg Arg Gly Arg Gly Arg Glu Arg Ala Arg Gly Gly Ser Arg Glu Arg
```

-continued

```
                355                 360                 365
Ala Arg Gly Arg Gly Arg Gly Arg Gly Glu Lys Arg Pro Arg Ser Pro
    370                 375                 380

Ser Ser Gln Ser Ser Ser Gly Ser Pro Pro Arg Arg Pro Pro Pro
385                 390                 395                 400

Gly Arg Arg Pro Phe Phe His Pro Val Gly Glu Ala Asp Tyr Phe Glu
                405                 410                 415

Tyr His Gln Glu Gly Gly Pro Asp Gly Glu Pro Asp Val Pro Pro Gly
            420                 425                 430

Ala Ile Glu Gln Gly Pro Ala Asp Asp Pro Gly Glu Gly Pro Ser Thr
        435                 440                 445

Gly Pro Arg Gly Gln Gly Asp Gly Gly Arg Arg Lys Lys Gly Gly Trp
    450                 455                 460

Phe Gly Lys His Arg Gly Gln Gly Gly Ser Asn Pro Lys Phe Glu Asn
465                 470                 475                 480

Ile Ala Glu Gly Leu Arg Ala Leu Leu Ala Arg Ser His Val Glu Arg
                485                 490                 495

Thr Thr Asp Glu Gly Thr Trp Val Ala Gly Val Phe Val Tyr Gly Gly
            500                 505                 510

Ser Lys Thr Ser Leu Tyr Asn Leu Arg Arg Gly Thr Ala Leu Ala Ile
        515                 520                 525

Pro Gln Cys Arg Leu Thr Pro Leu Ser Arg Leu Pro Phe Gly Met Ala
    530                 535                 540

Pro Gly Pro Gly Pro Gln Pro Gly Pro Leu Arg Glu Ser Ile Val Cys
545                 550                 555                 560

Tyr Phe Met Val Phe Leu Gln Thr His Ile Phe Ala Glu Val Leu Lys
                565                 570                 575

Asp Ala Ile Lys Asp Leu Val Met Thr Lys Pro Ala Pro Thr Cys Asn
            580                 585                 590

Ile Arg Val Thr Val Cys Ser Phe Asp Asp Gly Val Asp Leu Pro Pro
        595                 600                 605

Trp Phe Pro Pro Met Val Glu Gly Ala Ala Ala Glu Gly Asp Asp Gly
    610                 615                 620

Asp Asp Gly Asp Glu Gly Gly Asp Gly Asp Glu Gly Glu Glu Gly Gln
625                 630                 635                 640

Glu

<210> SEQ ID NO 2
<211> LENGTH: 50
<212> TYPE: PRT
<213> ORGANISM: Lymphotrophic herpes virus

<400> SEQUENCE: 2

Gly Arg Gly Arg Gly Arg Gly Arg Gly Arg Gly Gly Arg Pro Gly
1               5                   10                  15

Ala Pro Gly Gly Ser Gly Ser Gly Pro Arg His Arg Asp Gly Val Arg
            20                  25                  30

Arg Pro Gln Lys Arg Pro Ser Cys Ile Gly Cys Lys Gly Thr His Gly
        35                  40                  45

Gly Thr
    50

<210> SEQ ID NO 3
<211> LENGTH: 30
<212> TYPE: PRT
```

```
<213> ORGANISM: Lymphotrophic herpes virus

<400> SEQUENCE: 3

Ser Gly Ser Gly Pro Arg His Arg Asp Gly Val Arg Pro Gln Lys
 1               5                  10                  15

Arg Pro Ser Cys Ile Gly Cys Lys Gly Thr His Gly Gly Thr
            20                  25                  30

<210> SEQ ID NO 4
<211> LENGTH: 25
<212> TYPE: DNA
<213> ORGANISM: Artificial Sequence
<220> FEATURE:
<223> OTHER INFORMATION: A synthetic primer

<400> SEQUENCE: 4
tcacccacac tgtgcccatc tacga                                           25

<210> SEQ ID NO 5
<211> LENGTH: 25
<212> TYPE: DNA
<213> ORGANISM: Artificial Sequence
<220> FEATURE:
<223> OTHER INFORMATION: A synthetic primer

<400> SEQUENCE: 5
cagcggaacc gctcattgcc aatgg                                           25

<210> SEQ ID NO 6
<211> LENGTH: 26
<212> TYPE: DNA
<213> ORGANISM: Artificial Sequence
<220> FEATURE:
<223> OTHER INFORMATION: A synthetic probe

<400> SEQUENCE: 6
atgccctccc ccatgccatc ctgcgt                                          26

<210> SEQ ID NO 7
<211> LENGTH: 19
<212> TYPE: DNA
<213> ORGANISM: Artificial Sequence
<220> FEATURE:
<223> OTHER INFORMATION: A synthetic primer

<400> SEQUENCE: 7
cggaagccct ctggacttc                                                  19

<210> SEQ ID NO 8
<211> LENGTH: 21
<212> TYPE: DNA
<213> ORGANISM: Artificial Sequence
<220> FEATURE:
<223> OTHER INFORMATION: A synthetic primer

<400> SEQUENCE: 8
ccctgtttat ccgatggaat g                                               21

<210> SEQ ID NO 9
<211> LENGTH: 23
<212> TYPE: DNA
<213> ORGANISM: Artificial Sequence
<220> FEATURE:
<223> OTHER INFORMATION: A synthetic probe

<400> SEQUENCE: 9
```
tgtacacgca cgagaaatgc gcc                                          23

<210> SEQ ID NO 10
<211> LENGTH: 22
<212> TYPE: DNA
<213> ORGANISM: Artificial Sequence
<220> FEATURE:
<223> OTHER INFORMATION: A synthetic primer

<400> SEQUENCE: 10
ggcgcaagtg tgtgtaattt gt                                           22

<210> SEQ ID NO 11
<211> LENGTH: 17
<212> TYPE: DNA
<213> ORGANISM: Artificial Sequence
<220> FEATURE:
<223> OTHER INFORMATION: A synthetic primer

<400> SEQUENCE: 11
gggcgggcca agatagg                                                 17

<210> SEQ ID NO 12
<211> LENGTH: 22
<212> TYPE: DNA
<213> ORGANISM: Artificial Sequence
<220> FEATURE:
<223> OTHER INFORMATION: A synthetic probe

<400> SEQUENCE: 12
ctccagatcg cagcaatcgc gc                                           22

<210> SEQ ID NO 13
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 13
aggacctacg ctgccctaga                                              20

<210> SEQ ID NO 14
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 14
gctggtggtc cgcatgtttt                                              20

<210> SEQ ID NO 15
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 15
aggacagccg ttgccctagt ggtttcg                                      27

<210> SEQ ID NO 16
<211> LENGTH: 24
<212> TYPE: DNA

```
<213> ORGANISM: Artificial Sequence
<220> FEATURE:
<223> OTHER INFORMATION: A synthetic oligonucleotide

<400> SEQUENCE: 16
gtattcggct tgtccgctgt tttt                                              24

<210> SEQ ID NO 17
<211> LENGTH: 20
<212> TYPE: DNA
<213> ORGANISM: Artificial Sequence
<220> FEATURE:
<223> OTHER INFORMATION: A synthetic primer

<400> SEQUENCE: 17
gacggccagt gccaagctcg                                                   20

<210> SEQ ID NO 18
<211> LENGTH: 21
<212> TYPE: DNA
<213> ORGANISM: Artificial Sequence
<220> FEATURE:
<223> OTHER INFORMATION: A synthetic primer

<400> SEQUENCE: 18
gacgcaggca gttctatgcg g                                                 21
```

NON-CYTOTOXIC ORIP REPLICON

STATEMENT OF GOVERNMENT RIGHTS

The invention was made, at least in part, with a grant from the Government of the United States of America (grant CA22443 from the National Institutes of Health). The Government may have certain rights to the invention.

BACKGROUND OF THE INVENTION

Mammalian transcriptional activators have often been identified and characterized by transfection assays that require one or more templates to be transported and assembled in the nuclei of recipient cells. Recent efforts to understand the mechanisms of transcriptional activation on defined templates in vitro have helped define both cis-acting sequences and protein domains essential for gene regulation (Natarajan et al., 1999; Neely et al., 2002; Utley et al., 1994; Wallberg et al., 2000). However, limitations of this approach include the inability to assess contributions to transcription mediated by the trafficking of the transcription factors prior to or during chromatin assembly (Archer et al., 1992; Smith et al., 1997).

EBNA-1, encoded by Epstein-Barr virus (EBV), is a multifunctional protein essential for both EBV's extrachromosomal replication and positive and negative regulation of multiple viral promoters (Gahn et al., 1995; Lee et al., 1999; Sugden et al., 1989). EBNA-1 also positively regulates heterologous promoters when the family of repeats (FR) enhancer to which it binds in oriP is placed upstream of those promoters (Ceccarelli et al., 1998; Langle-Rouault et al., 1998; Mackey et al., 1999; Reisman et al., 1986; Wu et al., 2002). Studies of templates with or without FR microinjected into the cytoplasm or nuclei of cells that express EBNA-1 indicated that a significant contribution of EBNA-1 to the activation of transcription occurs in the cytoplasm (Langle-Rouault et al., 1998). Other studies have been interpreted to mean that EBNA-1 activates transcription on extrachromosomal but not integrated templates (Kang et al., 2001). These observations indicate that EBNA-1 likely uses multiple mechanisms to contribute to the support of transcription. If EBNA-1 can affect the transcription of integrated templates, EBNA-1 might regulate cellular genes during the latent phase of the EBV life cycle and, perhaps, in EBV-associated tumors.

EBV causes Burkitt's lymphoma (BL), which is endemic in Africa. BL is an aggressive B cell malignancy with a high proliferative rate that may be fatal within months if not treated promptly (Evens et al., 2002). Activation of the c-myc oncogene through reciprocal chromosomal translocations that juxtapose c-Myc to one of the Ig loci characterizes most BLs (Boxer et al., 2001). Additionally, many BLs carry point mutations in the p53 tumor suppressor gene or other defects in the p14ARF-MDM2-p53 pathway, or have p16INK4a genes activated by promoter methylation or homozygous deletion (Lindstrom et al., 2001; Lindstrom et al., 2002). Thus, BL involves multiple genetic events likely to promote cellular proliferation and inhibit apoptosis. In areas where BL is endemic, virtually all cases are associated with EBV (Niedobitek et al., 2001). Multiple viral genes are used by EBV to induce and maintain proliferation of infected B cells, but most of these genes are not expressed in BL tumors (Rowe et al., 1987), making it difficult to know what, if anything, EBV contributes to the survival of BL tumors.

Vectors derived from EBNA-1 are being considered for gene therapy in people (Banerjee et al., 1995; Calos, 1996; Cui et al., 2001; Franken et al., 1996; Harada et al., 2000; Phillips et al., 1999; Sclimenti et al., 1998; Stoll et al., 2001; Wohlgemuth et al., 1996). U.S. Pat. No. 4,686,186 discloses an EBV vector system which includes oriP and EBNA-1. However, EBNA-1, when overexpressed in a cell, is cytotoxic to that cell. This cytotoxicity limits its use in certain cell culture applications as well as in gene therapy. EBNA-1 may also be oncogenic (Wilson et al., 1996), further limiting its use. This increased risk of tumor development has been attributed in part to the transcriptional activation of host genes by EBNA-1 (Tsimbouri et al., 2002).

What is needed is an improved extrachromosomal vector system.

SUMMARY OF THE INVENTION

The invention provides a vector encoding a derivative of a wild-type protein of a lymphotrophic herpes virus, which wild-type protein corresponds to EBNA-1 of EBV. The derivative is noncytotoxic relative to the corresponding wild-type protein when expressed efficiently in a cell, e.g., a eukaryotic cell such as a vertebrate or mammalian cell, supports maintenance of an extrachromosomal template containing a DNA sequence corresponding to oriP of EBV, binds such a DNA sequence in a template, and activates transcription from such a template, but does not substantially activate transcription from an integrated template and/or host cell gene (a substantial activation of transcription is an activation of greater than 5-fold), e.g., a derivative of the invention may increase transcription from an integrated template and/or host cell gene by no more than 5-fold, for instance, less than 2-fold, relative to a control.

A "template" as used herein is a DNA molecule which is specifically bound by a wild-type protein of a lymphotrophic herpes virus, which wild-type protein corresponds to EBNA-1, as a result of the presence in that template of a DNA sequence which binds the wild-type protein with an affinity that is at least 10% that of the binding of a DNA sequence corresponding to oriP of EBV by the wild-type protein and from which template transcription is optionally initiated and/or enhanced after the protein binds and/or the maintenance of which template in a cell is enhanced. An "integrated template" is one which is stably maintained in the genome of the cell, i.e., integrated into a chromosome of that cell. An "extrachromosomal template" is one which is maintained stably maintained in a cell but which is not integrated into the chromosome. A "noncytotoxic" protein is one which, when efficiently expressed in a eukaryotic cell, i.e., a cell which is not infected with a lymphotrophic herpes virus, does not result in substantial cell death, e.g., more than 40% of the cells survive.

A "derivative" as used herein is a protein which is modified relative to a corresponding wild-type protein, i.e., the derivative has a modification which includes a deletion, insertion or substitution, or any combination thereof, of at least one amino acid in a region corresponding to the unique (nonrepetitive) region in LR1, which modification is associated with the lack of substantial transcriptional activation from an integrated template and the lack of cytotoxicity of the derivative. Like the corresponding wild-type protein, the derivative dimerizes and binds DNA containing a DNA sequence which binds the corresponding wild-type protein with an affinity that is at least 10% that of the binding of a DNA sequence corresponding to oriP of EBV by the wild-type protein, is not significantly degraded, e.g., by the ubiquitin/proteosome pathway and/or does not elicit a significant immune response associated with MHC class I presentation of antigen, and/or localizes to the nucleus when present in a cell or organism, as a result of the presence of a DNA binding and dimerization sequence, a repeat of Gly-Gly-Ala, Gly-Ala-Gly, Ala-Gly-Ala, Ala-Gly-Gly, Gly-Gly-Gly, or a combination thereof, and a nuclear localization sequence, respectively. "LR1" is a sequence in a lymphotrophic herpes virus which corresponds to residues 40 to 89 in EBNA-1 having SEQ ID NO:1, e.g., G RGRGRGRGRG GGRPGAPGGS GSGPRHRDGV RRPQKRPSCI GCKGTHGGT (SEQ ID NO:2), at least a portion of which in wild-type EBNA-1 is a transcriptional activation domain for integrated templates. The "unique region" of LR1 corresponds to residues 60 to 89 of EBNA-1. In one embodiment, a derivative of the invention lacks the following sequence SGSGPRHRDGVRRPQKRPSCI GCKGTHGGT (SEQ ID NO:3), or lacks a portion thereof. In one embodiment, the derivative has substantial identity, e.g., at least 80% or more, e.g., 85%, 90% or 95% and up to 100%, amino acid sequence identity, to a wild-type protein corresponding to EBNA-1, e.g., SEQ ID NO:1, for instance, substantial identity to residues from about residue 90 to the residue corresponding to the C-terminus of the wild-type protein, or any integer in between, and optionally also has substantial identity from residue 1 to about residue 20, and up to about residue 60, or any integer in between, of the corresponding wild-type protein. "About" as used herein with respect to a particular residue means within 5 residues of the specified residue, e.g., within 1, 2, 3, 4 or 5 residues of residue "X" corresponding to residue "X" in SEQ ID NO: 1.

As described herein, cells were established with integrated EBNA-1-responsive templates and it was shown that EBNA-1 activates transcription from these chromatin-embedded templates dose dependently. A mutational analysis of EBNA-1 identified a domain required for transcriptional activation of integrated templates, but not of transfected templates. The ability of EBNA-1 to activate transcription from both integrated and transfected templates can be inhibited by a derivative of EBNA-1 lacking the amino acids required for activation from integrated templates. EBNA-1's mode of activating transfected templates is therefore genetically distinct from that for activating integrated templates, which likely reflects either its trafficking or its control of template structure.

Thus, in one embodiment, the present invention provides a derivative of EBNA-1 lacking at least a portion of LR1, including a deletion of one or more, e.g., 2, 3, 4, 5, or more, residues between residues corresponding to residue 64 to 90 of EBNA-1, and optionally including a substitution of one or more, e.g., 2, 3, 4, 5 or more, amino acids, which derivative is not cytotoxic when expressed efficiently in cells, e.g., human cells, relative to EBNA-1 but supports extrachromosomal maintenance and replication of oriP containing vectors, and does not substantially activate transcription of host cell genes. Thus, vectors encoding such derivatives are excellent vectors for human gene therapy.

As also described herein, EBNA-1, a viral protein that is found in all EBV-associated malignancies, is required for the survival of EBV-positive Burkitt's lymphoma. Inhibition of EBNA-1 decreased survival of these tumor cells by inducing apoptosis. Expression of EBNA-1 in uninfected cells also can inhibit apoptosis induced by expression of p53 in the absence of the EBV genome. These findings demonstrate that EBNA-1 is important for the continued survival of EBV-associated Burkitt's lymphoma, and, by extension, for other B cell tumors with which EBV is associated. Further, EBV promotes survival of the tumor cells even long after their explantation. Thus, efficient inhibitors of EBNA-1's functions would likely prove useful in the therapy of EBV-associated malignancies.

Accordingly, the invention provides a recombinant plasmid comprising a DNA segment which encodes a noncytotoxic derivative of a wild-type protein from a lymphotrophic herpes virus, which wild-type protein corresponds to EBNA-1. The derivative lacks sequences present in the wild-type protein that activate transcription from integrated templates, but is capable of activating transcription from extrachromosomal templates having a DNA sequence which specifically binds the derivative as well as the wild-type protein, i.e., the DNA sequence corresponds to oriP of EBV.

In one embodiment, a recombinant vector is provided which includes a DNA segment which encodes a noncytotoxic derivative of a wild-type protein from a lymphotrophic herpes virus which corresponds to EBNA-1 of Epstein-Barr virus (EBV), which derivative activates transcription from an extrachromosomal template after the derivative binds a DNA sequence in the extrachromosomal template which binds the wild-type protein with an affinity at least 10% that of the binding of a DNA sequence which corresponds to oriP of EBV to the wild-type protein, which derivative lacks sequences present in the corresponding wild-type protein that activate transcription from an integrated template. Preferably, the derivative has a nuclear localization sequence and at least three consecutive tripeptide sequences, e.g., Gly-Gly-Ala, Gly-Ala-Gly, Ala-Gly-Ala, Ala-Gly-Gly, Gly-Gly-Gly, or any combination thereof. In one embodiment, the recombinant plasmid encodes a derivative of EBNA-1 having a deletion of at least 1, 2, 3, 4, 5, 6, 7, 8 or more residues, in the unique region of LR1, for instance, a deletion of at least 1, 2, 3, 4, 5, 6, 7, 8 or more residues, between residue 64 and up to residue 89. In one embodiment, the derivative activates transcription from extrachromosomal templates at levels at least 2%, e.g., 5%, 10%, 15%, 18%, 20% or more that of the corresponding wild-type protein, or increases transcription from extrachromosomal templates by at least 10-fold, 20-fold or more, relative to a negative control. In one embodiment, the recombinant plasmid further comprises the DNA sequence which binds the derivative and wild-type protein.

In another embodiment, a vector is provided. The vector includes a DNA segment which encodes a noncytotoxic derivative of a wild-type protein from a lymphotrophic virus, which wild-type protein corresponds to EBNA-1. The derivative lacks sequences present in the corresponding wild-type protein which activate transcription from an integrated template but is capable of activating transcription from an extrachromosomal template having a DNA sequence which binds the derivative (and wild-type protein) with an affinity that is at least 10% that of the binding of a DNA sequence which corresponds to oriP to the wild-type protein. The vector also includes the DNA sequence and a multiple cloning site (MCS) sequence suitable for cloning one or more heterologous polynucleotides, e.g., a heterologous open reading frame. In one embodiment of the invention, the vector is a plasmid which includes a plasmid backbone, a DNA segment encoding the derivative, a heterologous open reading frame, i.e., a nonlymphotrophic herpes virus open reading frame, optionally operably linked to a heterologous promoter, and a DNA sequence from a lymphotrophic herpes virus that is capable in cis of assisting in maintaining the plasmid in an eukaryotic host cell as a plasmid and when the derivative of the invention is expressed in the cell. It may also be desirable to include a marker gene, i.e., a gene or encoded gene product which is detectable or capable of detection, e.g., GFP or luciferase, or a selectable gene such as an antibiotic resistance gene, e.g., a hygromycin B resistance gene or neomycin phosphotransferase gene, in the plasmid, which marker gene or selectable gene is not present in the host cell prior to introduction of the plasmid. As the derivative of the wild-type protein from the lymphotrophic herpes virus acts in trans with the ori sequence, one can either position both the trans-acting and cis-acting fragments on a recombinant plasmid, or place the cis-acting fragment in the plasmid, and the trans-acting fragment in the genome of the cell, e.g., a cell not infected by EBV.

Also provided is a eukaryotic host comprising a recombinant vector. The recombinant vector includes a DNA segment encoding a noncytotoxic derivative of a wild-type protein from a lymphotrophic herpes virus, which wild-type protein corresponds to EBNA-1. The derivative lacks sequences present in the wild-type protein which activate transcription from an integrated template but activates transcription from an extrachromosomal template having a DNA sequence which binds the derivative (or wild-type protein) with an affinity that is at least 10% that of the binding of a DNA sequence which corresponds to oriP to the wild-type protein. In one embodiment, the derivative has a nuclear localization sequence and optionally at least three repeats of Gly-Gly-Ala, Gly-Ala-Gly, Gly-Gly-Gly, Ala-Gly-Ala, Ala-Gly-Gly, or any combination thereof. In yet another embodiment, a eukaryotic host is provided which has a recombinant plasmid with a plasmid backbone, a heterologous open reading frame, and a DNA sequence from a lymphotrophic herpes virus which supports maintenance and replication of the recombinant plasmid in a host which expresses a derivative of the invention. The DNA segment encoding a derivative of the invention may be part of the plasmid or introduced to the host by transformation or transduction of the host with another vector, e.g., a recombinant viral vector. The DNA sequence and DNA segment assist in maintaining the plasmid as a plasmid. In one embodiment, the host cell is a human B-lymphoblast.

Thus, a recombinant plasmid vector is provided which is useful to transform a wide range of eukaryotic cells and permit stable replication and expression thereof, a eukaryotic vector which permits stable replication of recombinant plasmids in latently infected eukaryotic cells, and an eukaryotic host which permits stable replication of the plasmid.

Further provided is a method to maintain and express a heterologous open reading frame in a cell. The method includes contacting a cell with a recombinant plasmid comprising a heterologous open reading frame and a DNA comprising a DNA sequence which binds a wild-type protein which corresponds to EBNA-1, wherein the affinity of the binding of a DNA sequence and the wild-type protein is at least 10% that of a DNA sequence which corresponds to oriP of EBV and the wild-type protein. The cell expresses a DNA segment which encodes a noncytotoxic derivative of a wild-type protein from a lymphotrophic herpes virus which corresponds to EBNA-1, which derivative lacks sequences present in the wild-type protein which activate transcription from an integrated template but which activates transcription from an extrachromosomal template having the DNA sequence. Preferably, the DNA sequence includes an origin of replication for Epstein-Barr virus, e.g., oriP, and the heterologous open reading frame codes for a protein of interest, e.g., a therapeutic or prophylactic protein which, when expressed in an effective amount in an organism such as a mammal provides a beneficial result, e.g., prevents, inhibits or treats a disease, e.g., one amenable to gene therapy, or induces a prophylactic or therapeutic immune response.

The invention also provides a method to maintain and express a heterologous open reading frame in a cell. The method includes contacting a cell with a recombinant plasmid comprising a heterologous open reading frame, a DNA sequence which binds the wild-type protein with an affinity that is at least 10% that of the binding of a DNA sequence which corresponds to oriP by the wild-type protein corresponding to EBNA-1, and a DNA segment which encodes a noncytotoxic derivative of a wild-type protein corresponding to EBNA-1, which derivative lacks sequences present in the wild-type protein which activate transcription from an integrated template, and which derivative activates transcription of the heterologous open reading frame.

Further provided is a therapeutic method. The method includes administering to a mammal in need of such therapy an effective amount of a recombinant plasmid comprising a heterologous open reading frame, a DNA sequence which binds the wild-type protein with an affinity of at least 10% relative to the binding of the wild-type protein to a DNA sequence, corresponds to oriP and binds a wild-type protein corresponding to EBNA-1, and a DNA segment which encodes a noncytotoxic derivative of a wild-type protein corresponding to EBNA-1, which derivative lacks sequences present in the wild-type protein which activate transcription from an integrated template, and which derivative activates transcription of the heterologous open reading frame. In one embodiment, the mammal has or is at risk of having cystic fibrosis or other diseases associated with aberrant expression of CFTR, e.g., decreased expression of a functional CFTR, and a recombinant plasmid of the invention which includes a heterologous open reading frame encoding a functional CFTR is administered to intranasally or intrabronchially The invention also provides a method to inhibit EBV-associated tumors. EBV-associated tumors include but are not limited to lymphomas and carcinomas. The method includes administering to a human having such a tumor an effective amount of a vector comprising a DNA segment encoding a noncytotoxic derivative of a wild-type protein from a lymphotrophic herpes virus which corresponds to EBNA-1 which derivative activates transcription from an extrachromosomal template after the derivative binds a DNA sequence in the extrachromosomal template which corresponds to oriP of EBV. In another embodiment, the derivative is administered to the human, e.g., in a delivery vehicle such as a liposome, a fusion polypeptide, or isolated protein. The derivative lacks sequences present in the wild-type protein which activate transcription of an integrated template.

BRIEF DESCRIPTION OF THE FIGURES

FIG. 11. Outlined are multiple events in the normal development of B cells that can lead to apoptosis (Defrance et al., 2002). Infection with EBV leads to survival of B cells with nonfunctional B cell receptors (BCR), avoiding apoptosis associated with peripheral B cell homeostasis, and results in latent infection within long-term memory B cells (Kuppers and Kanzler, 1997; Babcock et al., 1998). Inhibition of EBNA-1 results in apoptosis in all of the EBV-infected B cells tested.

FIG. 12. An exemplary EBNA-1 sequence (SEQ ID NO:1).

DETAILED DESCRIPTION OF THE INVENTION

I. Definitions

Figure 1A:
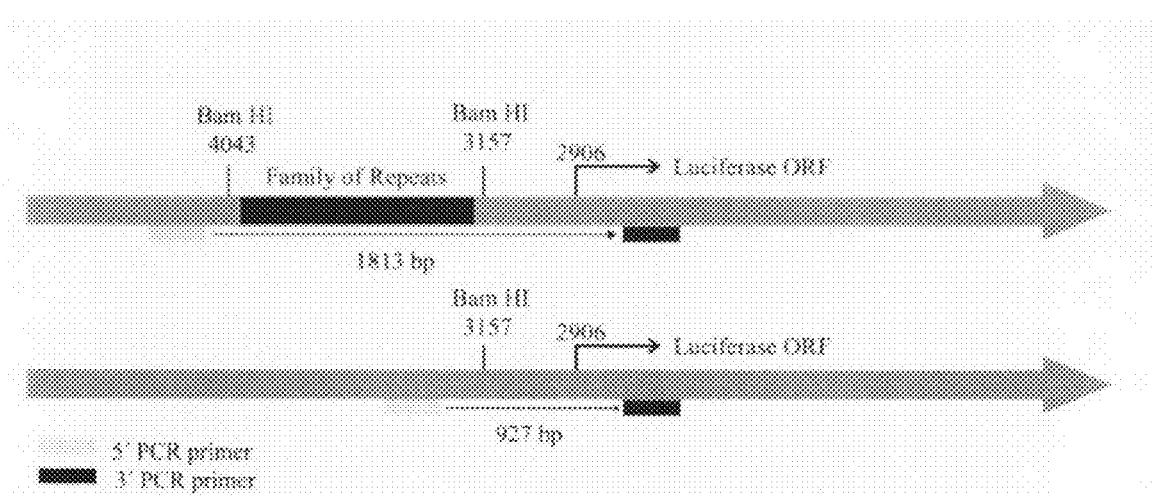
FIG. 1. Characterization of integrated template DNAs in clones of BJAB cells. (A) Structures of the two templates, FR-TK-luciferase and TK-luciferase, which were introduced into BJAB cells. The positions of the two primers used to characterize the templates and the sizes of their products generated by PCR are also shown. ORF, open reading frame. (B) Agarose gel resolving PCR products of DNAs isolated from two clones of BJAB cells into which FR-TK-luciferase (clones 2-12 and 2-14) was introduced and two clones into which TK-luciferase (clones 3-6 and 3-33) was introduced. The gel also includes the products derived by amplifying known amounts of the parental plasmids to serve as size markers and to permit estimates of the number of template molecules integrated into each cell.

An "origin of replication" ("ori") is a DNA sequence, e.g., in a lymphotrophic herpes virus, that when present in a plasmid in a cell is capable of maintaining linked sequences in the plasmid, and/or a site at or near where DNA synthesis initiates. An ori for EBV includes FR sequences (20 imperfect copies of a 30 bp repeat), and preferably DS sequences, however, other sites in EBV bind EBNA-1, e.g., Rep* sequences can substitute for DS as an origin of replication (Kirshmaier and Sugden, 1998). Thus, a DNA sequence which binds a protein corresponding to EBNA-1 includes FR, DS and Rep* sequences.

A "lymphotrophic" herpes virus is a herpes virus that replicates in a lymphoblast (e.g., a human B lymphoblast) and becomes a plasmid for a part of its natural life-cycle. After infecting a host, these viruses latently infect the host by maintaining the viral genome as a plasmid. Herpes simplex virus (HSV) is not a "lymphotrophic" herpes virus. Exemplary lymphotropic herpes viruses include, but are not limited to EBV, Kaposi's sarcoma herpes virus (KSHV); Herpes virus saimiri (HS) and Marek's disease virus (MDV).

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest for gene therapy. Vectors include, for example, viral vectors (such as adenoviruses, adeno-associated viruses (AAV), lentiviruses, herpesvirus and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described (see, e.g., Curiel et al., 1991).

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene includes at least a portion of an open reading frame of a gene which is partly or entirely heterologous (i.e., foreign) to the transgenic organism, or may represent an open reading frame or a portion thereof of a gene homologous to an endogenous gene of the organism, which portion optionally encodes a polypeptide with substantially the same activity as the corresponding full length polypeptide, e.g., wild-type polypeptide, or at least one activity of the corresponding full length polypeptide.

By "transgenic cell" is meant a cell containing a transgene. For example, a stem cell transformed with a vector containing an expression cassette can be used to produce a population of cells having altered phenotypic characteristics. A "recombinant cell" is one which has been genetically modified, e.g., by insertion, deletion or replacement of sequences in a nonrecombinant cell by genetic engineering.

The term "wild-type" or "native" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "transduction" denotes the delivery of a polynucleotide to a recipient cell either in vivo or in vitro, via a viral vector and preferably via a replication-defective viral vector.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

A "gene," "polynucleotide," "coding region," "sequence, " "segment," "fragment," or "transgene" which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

By "enhancer" is meant a nucleic acid sequence that, when positioned proximate to a promoter, confers increased transcription activity relative to the transcription activity resulting from the promoter in the absence of the enhancer domain.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

By "mammal" is meant any member of the class *Mammalia* including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide, polypeptide or virus refers to a nucleic acid sequence, peptide, polypeptide or virus that is identified and separated from at least one contaminant nucleic acid, polypeptide or other biological component with which it is ordinarily associated in its natural source. Isolated nucleic acid, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "peptide", "polypeptide" and protein" are used interchangeably herein unless otherwise distinguished.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of a selected sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

The term "selectively hybridize" means to detectably and specifically bind. Polynucleotides, oligonucleotides and fragments of the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest is at least 65%, and more typically with preferably increasing homologies of at least about 70%, about 90%, about 95%, about 98%, and 100%.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, 1972. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least about 80 percent sequence identity, preferably at least about 90 percent sequence identity, more preferably at least about 95 percent sequence identity, and most preferably at least about 99 percent sequence identity.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

A "protective immune response" and "prophylactic immune response" are used interchangeably to refer to an immune response which targets an immunogen to which the individual has not yet been exposed or targets a protein associated with a disease in an individual who does not have the disease, such as a tumor associated protein in a patient who does not have a tumor.

A "therapeutic immune response" refers to an immune response which targets an immunogen to which the individual has been exposed or a protein associated with a disease in an individual who has the disease.

The term "prophylactically effective amount" is meant to refer to the amount necessary to, in the case of infectious agents, prevent an individual from developing an infection, and in the case of diseases, prevent an individual from developing a disease.

The term "therapeutically effective amount" is meant to refer to the amount necessary to, in the case of infectious agents, reduce the level of infection in an infected individual in order to reduce symptoms or eliminate the infection, and in the case of diseases, to reduce symptoms or cure the individual.

"Inducing an immune response against an immunogen" is meant to refer to induction of an immune response in a naïve individual and induction of an immune response in an individual previously exposed to an immunogen wherein the immune response against the immunogen is enhanced.

II. Preparation of Expression Cassettes

To prepare expression cassettes for transformation herein, the recombinant DNA sequence or segment may be circular or linear, double-stranded or single-stranded. A DNA sequence which encodes an RNA sequence that is substantially complementary to a mRNA sequence encoding a gene product of interest is typically a "sense" DNA sequence cloned into a cassette in the opposite orientation (i.e., 3' to 5' rather than 5' to 3'). Generally, the DNA sequence or segment is in the form of chimeric DNA, such as plasmid DNA, that can also contain coding regions flanked by control sequences which promote the expression of the DNA in a cell. As used herein, "chimeric" means that a vector comprises DNA from at least two different species, or comprises DNA from the same species, which is linked or associated in a manner which does not occur in the "native" or wild-type of the species.

Aside from DNA sequences that serve as transcription units, or portions thereof, a portion of the DNA may be untranscribed, serving a regulatory or a structural function. For example, the DNA may itself comprise a promoter that is active in eukaryotic cells, e.g., mammalian cells, or in certain cell types, or may utilize a promoter already present in the genome that is the transformation target of the lymphotropic virus. Such promoters include the CMV promoter, as well as the SV40 late promoter and retroviral LTRs (long terminal repeat elements), e.g., the MMTV, RSV, MLV or HIV LTR, although many other promoter elements well known to the art may be employed in the practice of the invention.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The recombinant DNA to be introduced into the cells may contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, puro, hyg, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Exemplary reporter genes include the chloramphenicol acetyl transferase gene (cat) from Tn9 of $E.$ $coli$, the beta-glucuronidase gene (gus) of the uidA locus of $E.$ $coli$, the green, red, or blue fluorescent protein gene, and the luciferase gene. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, Sambrook et al. (1989) provides suitable methods of construction.

The recombinant DNA can be readily introduced into the host cells, e.g., mammalian, bacterial, yeast or insect cells, or prokaryotic cells, by transfection with an expression vector comprising the recombinant DNA by any procedure useful for the introduction into a particular cell, e.g., physical or biological methods, to yield a transformed (transgenic) cell having the recombinant DNA so that the DNA sequence of interest is expressed by the host cell. In one embodiment, at least one of the recombinant DNAs which is introduced to a cell is maintained extrachromosomally. In one embodiment, one recombinant DNA is maintained extrachromosomally while another is stably integrated into its genome.

Physical methods to introduce a recombinant DNA into a host cell include calcium-mediated methods, lipofection, particle bombardment, microinjection, electroporation, and the like. Biological methods to introduce the DNA of interest into a host cell include the use of DNA and RNA viral vectors. Viral vectors, e.g., retroviral or lentiviral vectors, have become a widely used method for inserting genes into eukaryotic, such as mammalian, e.g., human, cells. Other viral vectors useful to introduce genes into cells can be derived from poxviruses, e.g., vaccinia viruses, herpes viruses, adenoviruses, adeno-associated viruses, baculoviruses, and the like.

"Transfected," "transformed" or "transgenic" is used herein to include any host cell or cell line, which has been altered or augmented by the presence of at least one recombinant DNA sequence. The host cells of the present invention are typically produced by transfection with a DNA sequence in a plasmid expression vector, as an isolated linear DNA sequence, or infection with a recombinant viral vector.

To confirm the presence of the recombinant DNA sequence in the host cell, a variety of assays may be performed. Such assays include, for example, molecular biological assays well known to those of skill in the art, such as Southern and Northern blotting, RT-PCR and PCR; biochemical assays, such as detecting the presence or absence of a particular gene product, e.g., by immunological means (ELISAs and Western blots) or by other molecular assays.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the recombinant DNA segment is being expressed. Expression may be evaluated by specifically identifying the peptide products of the introduced DNA sequences or evaluating the phenotypic changes brought about by the expression of the introduced DNA segment in the host cell.

III. Polypeptides

The polypeptide derivatives of the invention can be synthesized in vitro, e.g., by the solid phase peptide synthetic method or by recombinant DNA approaches (see above). The solid phase peptide synthetic method is an established and widely used method, which is described in the following references: Stewart et al., 1969; Merrifield, 1963; Meienhofer, 1973; Bavaay and Merrifield, 1980; and Clark-Lewis et al., 1997. These polypeptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, chemically modified derivatives, of a given polypeptide derivative can be readily prepared. For example, amides of the polypeptide of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

Salts of carboxyl groups of a polypeptide of the invention may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the polypeptide may be prepared by utilizing an N-acyl protected amino acid for the final condensation, or by acylating a protected or unprotected polypeptide. O-acyl derivatives may be prepared, for example, by acylation of a free hydroxy polypeptide or polypeptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the polypeptide. Other amino-terminal modifications include aminooxypentane modifications (see Simmons et al., 1997).

A derivative of the invention is a polypeptide which, relative to a corresponding wild-type polypeptide, has a modified amino acid sequence. The modifications include the deletion, insertion or substitution of at least one amino acid residue in a region corresponding to the unique region of LR1 in EBNA-1, and may include a deletion, insertion and/or substitution of one or more amino acid residues in regions corresponding to other residues of EBNA-1, e.g., about residue 1 to about residue 40, residues about 90 to about 328 ("Gly-Gly-Ala" repeat region), residues about 329 to about 377 (LR2), residues about 379 to about 386 (NLS), residues about 451 to about 608 (DNA binding and dimerization), or residues about 609 to about 641, so long as the resulting derivative has the desired properties, e.g., dimerizes and binds DNA containing an ori corresponding to oriP, localizes to the nucleus, is not cytotoxic, and activates transcription from an extrachromosomal but does not substantially active transcription from an integrated template. Substitutions include substitutions which utilize the D rather than L form, as well as other well known amino acid analogs, e.g., unnatural amino acids such as α, α-disubstituted amino acids, N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3- carboxylic acid, penicillamine, ornithine, citruline, α-methyl-alanine, para-benzoyl-phenylalanine, phenylglycine, propargylglycine, sarcosine, ε-N,N,N-trimethyllysine, ε-N-acetyllysine, N-acetylserine, N-formylmethionine, 3-methylhistidine, 5-hydroxylysine, ω-N-methylarginine, and other similar amino acids and imino acids and tert-butylglycine.

Conservative amino acid substitutions are preferred—that is, for example, aspartic-glutamic as polar acidic amino acids; lysine/arginine/histidine as polar basic amino acids; leucine/isoleucine/methionine/valine/alanine/glycine/proline as nonpolar or hydrophobic amino acids; serine/threonine as polar or uncharged hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting polypeptide. Whether an amino acid change results in a functional polypeptide can readily be determined by assaying the specific activity of the polypeptide.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

The invention also envisions polypeptides with non-conservative substitutions. Non-conservative substitutions entail exchanging a member of one of the classes described above for another.

Acid addition salts of the polypeptide or of amino residues of the polypeptide may be prepared by contacting the polypeptide or amine with one or more equivalents of the desired inorganic or organic acid, such as, for example, hydrochloric acid. Esters of carboxyl groups of the polypeptides may also be prepared by any of the usual methods known in the art.

Analogs include structures having one or more peptide linkages optionally replaced by a linkage selected from the group consisting of: —CH$_2$NH—, —CH$_2$S—, —CH$_2$—CH$_2$—, —CH=CH-(cis and trans), —CH=CF-trans), —COCH$_2$—, —CH(OH)CH$_2$—, and —CH$_2$SO—, by methods known in the art and further described in the following references: Spatola, 1983; Spatola, 1983,; Morley, 1980; Hudson et al., 1979 (—CH$_2$NH—, CH$_2$CH$_2$—); Spatola et al., 1986 (—CH$_2$—S); Hann, 1982 (—CH—CH—, cis and trans); Almquist et al., 1980 (—COCH$_2$—); Jennings-White et al., 1982 (—COCH$_2$—); Szelke et al. European Appln. EP 45665 (—CH(OH)CH$_2$—); Holladay et al., 1983 (—C(OH)CH$_2$—); and Hruby, 1982 (—CH$_2$S—); each of which is incorporated herein by reference. A particularly preferred non-peptide linkage is —CH$_2$NH—. Such analogs may have greater chemical stability, enhanced pharmacological properties (half-life, absorption, potency, efficacy, etc.), altered specificity (e.g., a broad-spectrum of biological activities), reduced antigenicity, and be economically prepared.

IV. Compositions, Formulations and Uses of the Vectors

The vectors of the invention may be employed in vitro, ex vivo, i.e., cells to be introduced to an eukaryotic organism, e.g., a mammal, or in vivo, e.g., as a gene transfer vector useful to transfer therapeutic or prophylactic gene products. The amount of vector(s) administered will vary depending on various factors including, but not limited to, the vector(s) chosen, the condition or disease, and whether prevention or treatment is to be achieved. Administration of the vectors in accordance with the present invention may be continuous or intermittent. Both local and systemic administration is contemplated.

Recombinant viruses such as recombinant retroviruses, lentiviruses, adenoviruses, and adeno-associated viruses (AAV), plasmid vectors or liposome-polynucleotide complexes, may be employed to deliver a polynucleotide encoding a derivative of the invention to a cell, and recombinant viruses such as recombinant herpes viruses, plasmid vectors or liposome-polynucleotide complexes, may be employed to deliver a vector comprising DNA sequence corresponding to oriP and a heterologous open reading frame to a cell. The use of plasmid- or liposome-based vectors, e.g., oriP-based vectors, and/or vectors encoding the Gly-Gly-Ala repeat of EBNA-1 permit large fragments of DNA to be introduced to a cell and maintained extrachromosomally, replicated once per cell cycle, partitioned to daughter cells efficiently, and elicit substantially no immune response. In particular, EBNA-1, the only viral protein required for the replication of the oriP-based expression vector, does not elicit a cellular immune response because it has developed an efficient mechanism to bypass the processing required for presentation of its antigens on MHC class I molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

One application of oriP-based expression vectors is the delivery of a wild-type gene to cells in which both alleles for the gene are defective. An oriP plasmid can be constructed which supports expression of EBNA-1, the gene of interest, and a selectable marker. Lei et al. (1996) used an oriP-based vector to deliver the cystic fibrosis transmembrane conductance regulator (CFTR) gene to transformed human airway epithelial cells defective in cAMP-dependent chloride transport. Transfection of this vector into the indicated cells led to the restoration of cAMP-dependent chloride transport. The rate of loss for oriP plasmids is a function of the number of cell cycles through which a host cell passes without selection (Kirchmaier et al., 1995; Wohlgemuth et al., 1996). Generally, the plasmids are lost at about 3%/cell/generation in the absence of selection. Because most cells in adults proliferate slowly or not at all, oriP/EBNA-1 vectors are likely to be maintained in them for long times. Therefore, airway epithelial cells in adults are likely ideal targets for this type of therapy. If oriP plasmids are targeted to rapidly dividing cells, it may be necessary to re-administered them periodically or provide the cells which carry the oriP plasmids with a selective advantage.

OriP-based expression vectors can also be used to target genes to tumour cells. Hirai et al. (1997) developed a system to target therapeutic agents to EBV-positive cells. They designed an oriP plasmid which contained the HSV thymidine kinase gene driven by its native promoter. EBNA-1-positive and -negative cells were transfected with this plasmid via envelope proteins from inactivated haemagglutinating virus of Japan (HVJ, or Sendai virus), treated with 30 mM gancyclovir at 3 days post-transfection and monitored for viability at different time points. After 3 days of treatment with gancyclovir, less than 10% of the EBNA-1-positive cells were viable, whereas toxicity was not detected in EBNA-1-negative cell lines. This approach, in which HVJ-liposomes are used to target oriP plasmids to EBNA-1-positive cells, may prove valuable for treating EBV-associated malignancies. HVJ-liposomes have been successfully used to deliver marker genes into bone marrow cells and human primary fibroblasts (Satob et al., 1991) and so are a delivery system for oriP-based expression vectors.

To introduce a vector into target cells other than B lymphocytes, inoculation of naked DNA, e.g., using electroporation, iontophoresis or particle-mediated delivery, complexing the DNA with polycations such as cationic lipids or cationic polymers (Dubensky et al., 1984; Felgner et al., 1989; Perales et al., 1994; Wolff et al., 1990) or polyanions (Kaneda, 2001), e.g., liposome-mediated gene transfer, may be employed. These methods may be employed to deliver the gene repeatedly if rapidly proliferating cells are the requisite targets for gene transfer.

OriP-based vectors not only are potentially effective tools in gene therapy, but may also be used to advantage in cell culture. An oriP vector into which a gene of interest has been cloned can be maintained extrachromosomally in many mammalian cells which express EBNA-1 (Yates et al., 1984). The EBNA-1 moiety of this replicon can be expressed either as a gene integrated into the host cell or as a gene incorporated into the vector. The former approach has the advantage of a 10- to 100-fold increase in the number of transfected cells that support extrachromosomal replication of the oriP vector (Peterson et al., 1991). The latter approach provides versatility to the use of a single vector in many cell types.

OriP/EBNA-1 replicons have been used to study gene expression with at least three different goals. First, the expressed genes have been dissected genetically to elucidate their functions via the phenotypes they induce. The efficient expression of genes from oriP vectors facilitates these experiments (Langle-Rouault et al., 1998; Evans et al., 1997). Second, the transcriptional regulation of genes expressed from oriP vectors has been analysed genetically. These analyses allow mutagenesis of cis-acting elements within a promoter and measurements of transcription from the promoter in a population of cells which have been selected to maintain the plasmid replicon. Third, the plasmid nature of oriP vectors allows their ready isolation from transfected cells and has permitted the development of selections in mammalian cells for expressed genes which compensate for defects in the recipient cells.

A major application of genes expressed from oriP vectors has been to analyse genetically cis- and trans-acting elements of EBV itself. Genetic studies of EBNA-1, EBNA-2, LMP-1, oriP and oriLyt have all been conducted with oriP expression vectors. This use of oriP vectors has been extended to the study of cellular genes too. For example, the L1 retrotransposon has been introduced into an oriP vector and its rate of transposition to the host cell genome measured (Moran et al., 1996). Mutations introduced into an open reading frame of the retrotransposon affected the rate of retrotransposition and confirmed the role of this open reading frame in retrotransposition.

The chromatin structure of genes inserted into oriP vectors, as exemplified by the HIV provirus, appears similar or identical to that of genes integrated into the cellular genome (Stanfield-Oakley et al., 1996). These observations make oriP/EBNA-1 vectors desirable vehicles for the analysis of the regulation of gene expression. Stretches of 50 kbp of DNA from the human c-myc locus have been cloned into a F-factor plasmid which contains oriP, propagated in E. coli, purified, and then introduced into EBV-positive cells which provide EBNA-1 in trans. Cis-acting enhancers from the immunoglobulin locus were shown to activate transcription of c-myc even when the enhancers were located 30 kbp away (Mautner et al., 1996).

A third application of oriP/EBNA-1 plasmids is to select for expressed genes in a library of oriP vectors which carry a cDNA or genomic DNA that complement a defect in a recipient cell or otherwise provide the recipient cell a selective advantage. This application has been used effectively to search for wild-type genes which when mutant render cells susceptible to efficient killing with ultraviolet light. The wild-type cDNA of a gene mutated in cells of a patient with xeroderma pigmentosum group C (XP-C) was recovered on an oriP vector after its selection in XP-C cells exposed to UV-light in cell culture (Legerski et al., 1992). An analogous selection has been used successfully to isolate a wild-type cDNA of the CSA gene mutated in hereditary Cockayne Syndrome. This application will also be rendered more facile by the use of YAC and BAC libraries in which the vectors have incorporated oriP (Simpson et al., 1996; Henning et al., 1995).

For gene therapy, the vectors of the invention may be introduced to any mammal, e.g., a mammal having symptoms of a genetically-based disorder, an acquired disorder or an infectious disease which is amenable to gene-based therapy, including but not limited to bovine, ovine, equine, caprine, canine, feline, and porcine, as well as primates, particularly humans.

In one embodiment, gene transfer in vivo is obtained by introducing an expression vector into the mammalian host, either as naked DNA, recombinant virus or DNA complexed to charged carriers, e.g., cationic lipid carriers. The vectors may provide for integration into the host cell genome for stable maintenance of the transgene encoding the derivative of the invention or for episomal expression of a prophylactic or therapeutic transgene. The introduction into the mammalian host may be by any of several routes, including intravenous or intraperitoneal injection, intratracheally, intrathecally, parenterally, intraarticularly, intranasally, intramuscularly, topical, transdermal, application to any mucous membrane surface, corneal instillation, and the like. For instance, an expression vector is introduced into a circulating bodily fluid or into a body orifice or cavity, such as lung, colon, vagina, and the like, or intrathecal administration, which may result in wide dissemination of the vector following such routes of administration. In one embodiment, aerosol administration is employed to introduce a vector into a body orifice or cavity. Any physiologically acceptable medium may be employed for administering the DNA, recombinant virus or lipid carriers, such as deionized water, saline, phosphate-buffered saline, 5% dextrose in water, and the like, depending upon the route of administration. Other components may be included in the formulation such as buffers, stabilizers, biocides, and the like.

The amount of naked DNA, recombinant virus or complexes used is an amount sufficient to provide for adequate dissemination to a variety of tissues after entry of the DNA, recombinant virus or complexes into the bloodstream and to provide for a therapeutic or prophylactic level of expression in at least some transfected or infected tissues. A therapeutic or prophylactic level of expression is a sufficient amount of expression to prevent, treat or palliate a disease or infection of the mammal.

The formulations and compositions described herein may also contain other ingredients such as antimicrobial agents, or preservatives. Furthermore, the active ingredients may also be used in combination with other therapeutic agents Kits of the invention will generally include the DNA either as naked DNA or complexed to lipid carriers, and/or an isolated derivative of the invention. Additionally, lipid carriers may be provided in a separate container for complexing with the provided DNA. The DNA either for direct administration or for complexing with lipid carriers, or the lipid carrier/DNA complexes, and/or an isolated derivative of the invention may be present as concentrates which may be further diluted prior to use or they may be provided at the concentration of use, where the vials may include one or more dosages. Conveniently, single dosages may be provided in sterile vials so that the physician or veterinarian may employ the vials directly, where the vials will have the desired amount and concentration of agents. Thus, a vial may contain the DNA, the DNA/lipid carrier and/or an isolated derivative of the invention in appropriate proportional amounts. When the vials contain the formulation for direct use, usually there will be no need for other reagents for use with the method.

For parenteral administration, sterile liquid pharmaceutical compositions, solutions or suspensions can be utilized by, for example, intraperitoneal injection, subcutaneous injection, intravenously, or topically. The vectors can be also be administered intravascularly or via an implantable device, e.g., a needle, catheter, shunt, or stent.

In addition, the vectors can be formulated for inhalation. The liquid carrier for pressurized compositions can be halogenated hydrocarbon or other pharmaceutically acceptable propellent. Such pressurized compositions are typically lipid encapsulated or associated for delivery via inhalation. For administration by intranasal or intrabronchial inhalation or insufflation, the vectors may be formulated into an aqueous or partially aqueous solution, which can then be utilized in the form of an aerosol, for example, for treatment of conditions affecting the respiratory tract, such as cystic fibrosis.

For viral delivery, vector particles which have been purified or concentrated may be preserved by first adding a sufficient amount of a formulation buffer to the media containing the particles, in order to form an aqueous suspension. The formulation buffer may be an aqueous solution that contains a saccharide, a high molecular weight structural additive, and a buffering component in water. As utilized within the context of the resent invention, a "buffering compound" or "buffering component" should be understood to refer to a substance that functions to maintain the aqueous suspension at a desired pH. The aqueous solution may also contain one or more amino acids.

The particles can also be preserved in a purified form. More specifically, prior to the addition of the formulation buffer, the crude particles may be clarified by passing it through a filter, and then concentrated, such as by a cross flow concentrating system.

The crude particle preparation can also be purified by ion exchange column chromatography. In general, the crude particle preparation is clarified by passing it through a filter, and the filtrate loaded onto a column containing a highly sulfonated cellulose matrix. The particles are eluted from the column in purified form by using a high salt buffer. The high salt buffer is then exchanged for a more desirable buffer by passing the eluate over a molecular exclusion column. A sufficient amount of formulation buffer is then added, as discussed above, to the purified vector particle and the aqueous suspension is either dried immediately or stored, preferably at −70° C. The aqueous suspension in crude or purified form can be dried by lyophilization or evaporation at ambient temperature. Within the evaporative method, water is removed from the aqueous suspension at ambient temperature by evaporation. Within one embodiment, water is removed through spray drying.

The aqueous solutions used for formulation may be composed of a saccharide, high molecular weight structural additive, a buffering component, and water. The solution may also include one or more amino acids. The combination of these components act to preserve the activity of the particles upon freezing and lyophilization, or drying through evaporation.

The lyophilized or dehydrated viruses may be reconstituted using a variety of substances, but are preferably reconstituted using water. Particles of the present invention may be administered to a wide variety of locations including, for example, into sites such as the cerebral spinal fluid, bone marrow, joints, arterial endothelial cells, rectum, buccal/sublingual, vagina, the lymph system, to an organ selected from the group consisting of lung, liver, spleen, skin, blood and brain, or to a site selected from the group consisting of tumors and interstitial spaces. Within other embodiments, the vector particle may be administered intraocularly, intranasally, sublingually, orally, topically, intravesically, intrathecally, topically, intravenously, intraperitoneally, intracranially, intramuscularly, or subcutaneously.

V. Exemplary Genes Useful in the Vectors of the Invention

A gene delivery vector may be designed to express any open reading frame, including but not limited to a therapeutic protein capable of preventing, inhibiting, stabilizing or reversing an inherited or noninherited genetic defect in metabolism, immune regulation, hormonal regulation, enzymatic or membrane associated structural function, or a prophylactic protein. Diseases which are amenable to treatment by a gene delivery vector of the invention include but are not limited to cystic fibrosis, Parkinson's disease, thalassemia, phenylketonuria, Lesch-Nyhan syndrome, severe combined immunodeficiency (SCID), Duchenne's Muscular Dystrophy, inherited emphysema, hypercholesterolemia, adenosine deaminase deficiency, β-globin disorders, α1 antitrypsin (AAT) deficiency, hemophilia A, hemophilia B, Gaucher's disease, storage disease mucopolysaccharidosis type VII, hereditary lactose intolerance, diabetes, and leukemia, and the therapeutic gene may encode factor VIII, factor IX, factor V, adenosine deaminase, e.g., to treat leukemia arising from retroviral insertion (Schmidt et al., 2003), lactase, β-glucuronidase, antithrombin III, protein C, prothrombin, or thrombomodulin.

In addition the vectors can be used to produce anti-sense nucleic acids in cells. Antisense therapy involves the production of nucleic acids that bind to a target nucleic acid, typically an RNA molecule, located within cells. Antisense therapy generally employs oligonucleotides that are complementary to mRNA molecules ("sense strands") which encode a cellular product. Exemplary modes by which sequences can be targeted for therapeutic applications include: blocking the interaction of a protein with an RNA sequence (e.g., the interaction of RNA virus regulatory proteins with their RNA genomes); and targeting sequences causing inappropriate expression of cellular genes or cell proliferation (e.g., genes associated with cell cycle regulation; genetic disorders; and cancers (protooncogenes)). Exemplary potential target sequences are protooncogenes, oncogenes/tumor suppressor genes, transcription factors, and viral genes.

In addition, the vectors of the present invention can be used to deliver DNA sequences encoding catalytic RNA molecules into cells. For example, DNA sequences encoding a ribozyme of interest can be cloned into a vector of the present invention. Such a ribozyme may be a hammerhead ribozyme capable of cleaving a viral substrate, or an undesirable messenger RNA, such as that of an oncogene. The DNA-encoding ribozyme sequences can be expressed in tandem with tRNA sequences, with transcription directed from, for example, mammalian tRNA promoters.

Thus, exemplary gene products of interest for use with the vectors of the invention include but are not limited to, DNA sequences which code for an antisense or ribozyme sequence such as one to HIV-REV or a BCR-ABL sequence, code for proteins such as transdominant negative mutants which specifically prevent the integration of HIV genes into the host cell genomic DNA, replication of HIV sequences, translation of HIV proteins, processing of HIV mRNA, or virus packaging in human cells; code for wild-type conductance regulator (CFTR), wild-type p53, granulocyte macrophage colony stimulating factor (GM-CSF), as well as the LDL (low density lipoprotein) receptor, apo(a), phenylalanine hydroxylase, ornithine transcarboxylase (OTC), molecules which have superoxide dismutase activity, endothelial prostaglandin synthase, alpha-1 antitrypsin, erythropoietin, cytokines, e.g., IL-1, IL-2, IL-3, IL-4, IL-5, IL-6, IL-8, IL-9, IL-10, IL-11, IL-12, IL-13, IL-14, IL-15, and IL-18, the gamma chain of cytokine receptors (Kennedy and Sugden, 2003), alpha interferon, gamma interferons, G-CSF or tumor necrosis factors (TNFs), polypeptide or peptide hormones, blood clotting factors, phosphorylases, and kinases. Representative examples of antisense sequences include, but are not limited to, antisense thymidine kinase, antisense dihydrofolate reductase, antisense IL-1 receptor, antisense BER2, antisense ABL, antisense Myc, and antisense ras, as well as antisense sequences which block any of the enzymes in the nucleotide biosynthetic pathway, or antisense sequences for influenza virus, HIV, HSV, HPV, CMV, and HBV. Proteins of therapeutic interest for the treatment of coronary heart disease and congestive heart failure include fibroblast growth factors such as FGF-2 and beta adrenergic receptors.

Prophylactic compositions may comprise a vector encoding a gene product for which is desirable to produce an immune response, e.g., a response to pathogens including viruses, e.g., gB of HSV, bacteria, yeast and fungi, or tumor antigens.

The invention will be further described by the following nonlimiting examples.

EXAMPLE I

Materials and Methods

Cell culture. The BJAB cell line, an EBV-negative Burkitt's lymphoma derivative, has been previously described (Steinitz et al., 1975). Cells were grown in RPMI 1640 medium (GibcoBRL) supplemented with 10% fetal bovine serum, 40 U of penicillin/ml, and 50 μg of streptomycin/ml at 37° C. in a 5% $CO_2$ humidified atmosphere.

Transfection and cloning. Electroporation of $5 \times 10^6$ cells was performed in 500 μl of complete medium with 250 V and a capacitance of 960 μF using a Bio-Rad (Hercules, Calif.) generator. BJAB cells with integrated EBV-responsive templates were established by cotransfecting DNAs expressing the puromycin resistance gene and DNAs expressing either FR-thymidine kinase (TK)-luciferase or TK-luciferase. Forty-eight hours posttransfection, cells were plated in limiting dilutions on 96-well plates in the presence of 1 μg of puromycin/ml. The cells were grown for 2 to 3 weeks, and the proliferating cells were counted. Those microwell cultures with a >90% probability of being derived from single cells were expanded and screened for the presence of luciferase activity. All clones that demonstrated a background luciferase activity of $<10^4$ relative light units (RLU) per $10^5$ cells were expanded and tested for responsiveness to EBNA-1. Once isolated, the clones were propagated continuously in the presence of 1 μg of puromycin/ml.

PCR. Clones of cells resistant to puromycin were screened by PCR for the integration of FR-TK-luciferase or TK-luciferase. Colonies identified in the cloning assay were expanded, and total cellular DNA was extracted from $5 \times 10^6$ cells using the DNeasy kit from Qiagen (Valencia, Calif.). The protocol was modified to include a 4 hour proteinase K digestion instead of the 15 minute digestion suggested by the manufacturer. After quantification, 50 ng of DNA was subjected to PCR in the presence of 5 U of Herculase polymerase (Invitrogen, Carlsbad, Calif.) for 25 cycles in a 25 μl total volume. The primers used for the PCR were 5'-GAC GGC CAG TGC CAA GCT CG-3' (sense sequence; SEQ ID NO:17) and 5'-GAC GCA GGC AGT TCT ATG CGG-3' (antisense sequence; SEQ ID NO: 18).

Plasmids. Some of the derivatives of EBNA-1 used in this study have been previously described (Mackay et al., 1999). Mutants of EBNA-1 with deletions of amino acids 65 to 89 or 359 to 369 were constructed using whole-plasmid PCR. Amino acids 65 to 89 were replaced with a unique NgoMIV restriction site encoding a glycine and an alanine, while amino acids 359 to 369 were replaced with a unique XbaI site encoding an arginine and a serine. The PCR products were purified and digested with either NgoMIV or XbaI, ligated, and propagated in *Escherichia coli*. Recovered DNAs were sequenced within the EBNA-1 open reading frame to ensure accuracy of the PCR product. The amino acid composition from 396 to 455 of the shuffled joining domain (JD) derivative remained the same as the composition within wild-type EBNA-1, but its sequence had been randomized (J. Wang, personal communication).

Reporter plasmids expressing FR-TK-luciferase, TK-luciferase, or FR-TK-CAT have been previously described (Middleton et al., 1992). Briefly, each plasmid with or without FR contains the herpes simplex virus TK promoter driving the expression of either the luciferase or chloramphenicol acetyltransferase (CAT) gene.

Retroviral propagation and infection. The retroviruses used in this study are derived from a vesicular stomatitis virus G protein-pseudotyped murine leukemia virus (Ory et al., 1996). To construct a retrovirus expressing wild-type EBNA-1, the parent retroviral plasmid encoding β-galactosidase (lacZ) was digested with AgeI and AvrII and blunted with the Klenow fragment of DNA polymerase I. The desired fragment was purified and ligated with the open reading frame of EBNA-1 derived from digesting a plasmid encoding EBNA-1 with BglII and XhoI treated with the Klenow fragment. The orientation of the insert within the recovered DNA was confirmed by digestion with restriction endonucleases. Retroviruses were generated by transfecting 293-HEK cells with 3 μg of a plasmid encoding the Gag-Pol elements, 1 µg of plasmids encoding the vesicular stomatitis virus G protein, and 5 µg of a plasmid carrying the retroviral backbone encoding either β-galactosidase or EBNA-1 using the Lipofectamine 2000 reagent (Invitrogen) as described by the manufacturer. Twenty-four hours post-transfection, the culture medium was supplemented with 50 mM HEPES. On days 2 to 4 posttransfection, the culture supernatant was collected, filtered through a 0.45 µm pore size filter, and stored at −80° C. The titers of the viral stocks were estimated by infecting 293-HEK cells plated at $5 \times 10^4$ per well of a 24-well plate with 1:5 serial dilutions of viral stocks. Infected cells were identified by the expression of green fluorescent protein (GFP), also encoded by each of the viruses from an internal ribosomal entry site, and titers were calculated according to a Poisson distribution.

BJAB cells growing exponentially were centrifuged and resuspended at $5 \times 10^6$ per ml prior to infection. One milliliter of cells was then infected at a multiplicity of infection of 1 by incubating the suspension in complete medium supplemented with 50 mM HEPES and 100 µg of Polybrene (Sigma, St. Louis, Mo.)/ml for 1 hour at 4° C. with gentle rocking. After the incubation period, the cells were collected by centrifugation, resuspended in 10 ml of complete medium, and incubated at 37° C. Forty-eight hours postinfection, the infected cells were sorted on a FACS-Vantage or FACS-DIVA (Becton Dickinson, San Jose, Calif.), enriching for the green population of cells. Luciferase assays were performed on $10^5$ sorted green cells as described below.

Reporter assays. Forty-eight hours posttransfection, the efficiency of transfection was estimated by counting GFP-positive cells, and the transfected cells were collected by centrifugation, washed with phosphate-buffered saline, and resuspended in cell culture lysis buffer at a concentration of $5 \times 10^4$ per µl. A total of 20 µl of lysed cells was analyzed for luciferase activity (Mitchell et al., 1995). RLU were normalized to the efficiency of transfection by subtracting the RLU obtained from $10^6$ untransfected cells from the RLU obtained from $10^6$ transfected cells and dividing by the transfection efficiency. A total of $10^5$ cells was assayed for CAT activity using thin-layer chromatography as previously described (Kaykas et al., 2001). Chloramphenicol-labeled with $^{14}C$ was purchased from NEN-Life Science (Boston, Mass.). The CAT activity was normalized by dividing the percent acetylated chloramphenicol by the total number of transfected cells and multiplying the resulting number by $10^6$. The normalized numbers are referred to as acetylation units.

Prior to using the CAT assay, the linear range of the assay was established with EBV-negative BJAB cells transfected with a CAT reporter with or without vector expressing EBNA-1. A range of cellular lysates was used in the assay, and the acetylated forms of CAT were separated from the unacetylated forms by thin-layer chromatography. The thin-layer chromatography plates were exposed to a PhosphorImager screen, and the optical densities (OD) of the bands were quantified by ImageQuant version of 5.0 (Molecular Dynamics, Sunnyvale, Calif.). The CAT assay was found to be linear from an OD of $10^4$ to $10^6$ U. The measurements of CAT activity obtained from cells transfected with various derivatives of EBNA-1 were within this linear range.

All reporter assay results are presented as increases (n-fold) in transcription. To calculate the increase, the activity detected from cells lacking the reporter gene was subtracted from the activity obtained from cells in the presence of the reporter gene. The increase in transcription was calculated by dividing the RLU or acetylation units obtained from the cells transfected with the various derivatives of EBNA-1 by the RLU or acetylation units obtained from cells transfected with the empty vector.

Western blot analysis. Forty-eight hours after transfection, the cells were counted and the efficiency of transfection was measured by the expression of GFP. The cells were washed with phosphate-buffered saline, resuspended at $2 \times 10^4/\mu l$ in 1× sample buffer (0.05% sodium dodecyl sulfate, 2 mM Tris-HCl [pH 6.8], 0.1% 2-mercaptoethanol, 0.2% glycerol, and 0.02% bromophenol blue), and incubated for 30 minutes on ice. The lysates were sonicated and incubated at 95° C. for 10 minutes. Protein lysates approximately equivalent to $5 \times 10^5$ cells were separated in an 8% sodium dodecyl sulfate-polyacrylamide gel, transferred electrophoretically to a nitrocellulose membrane (Bio-Rad), and blocked overnight with 5% nonfat dry milk. For the primary antibody, a rabbit antiserum affinity purified against the C-terminus of EBNA-1 was used to detect wild-type EBNA-1 and the six derivatives. A murine monoclonal antibody conjugated to fluorescein isothiocyanate was used to detect β-actin (Sigma, St. Louis, Mo.). For the secondary antibody, goat anti-rabbit antibody conjugated to peroxidases was used and detected with the ECL Western blotting analysis system (Amersham Pharmacia Biotech, Piscataway, N.J.).

The intensity of each protein band was estimated using ImageQuant version 5.0 software. The loading error was corrected by normalizing to the intensity of β-actin detected in cells transfected with wild-type EBNA-1. The OD of each derivative of EBNA-1 was confirmed to be in the linear range by using different exposures of the membrane to film, and this signal was multiplied by the β-actin correction factor. The β-actin-corrected number was divided by the total number of transfected cells loaded per lane, and the amount of EBNA-1 derivative detected relative to wild-type EBNA-1 was expressed as the OD per transfected cell.

Statistical analysis. All statistical analyses were performed using Mstat version 3.21 (N. Drinkwater, McArdle Laboratory for Cancer Research, University of Wisconsin Medical School), which is available at http://mcardle.oncology.wisc.edu/mstat. The nonparametric Wilcoxon rank sum test was used in all cases unless otherwise indicated.

Results

Figure 1B:
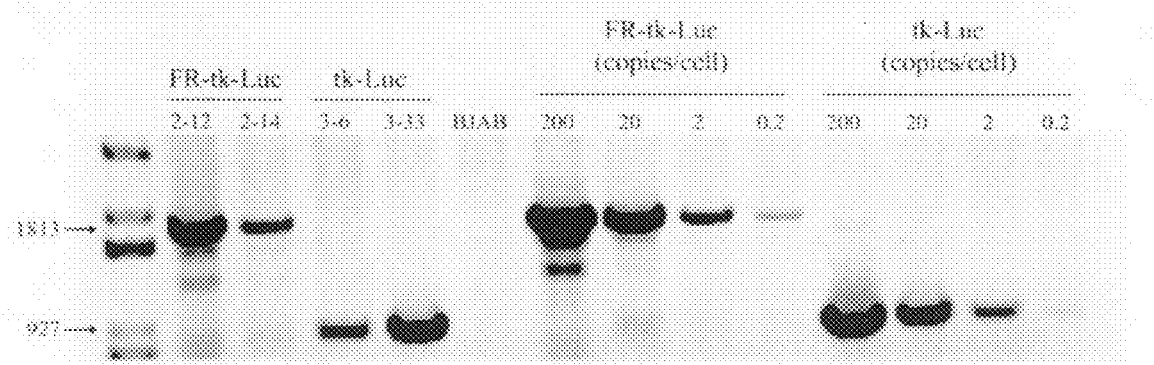

EBNA-1 activates transcription from nuclear templates dose dependently. In order to determine unambiguously if EBNA-1 can activate transcription from templates within the nucleus, multiple clones with integrated templates were established. BJAB cells, an EBV-negative Burkitt's lymphoma-derived cell line, were used as host cells, and PCR was used to screen the derived clones for integration of the luciferase gene expressed from the HSV-1 TK promoter plus or minus FR (FIG. 1A). FIG. 1B shows an ethidium bromide-stained 1% agarose gel that separates amplified DNA from two clones with FR-TK-luciferase and two clones with TK-luciferase integrated into the cellular DNA. A standard curve is shown, demonstrating the sensitivity of the assay to be less than one copy of DNA per cell. A total of 80 puromycin-resistant clones was initially isolated, and of these, 20 had the luciferase gene present as shown by either PCR or luciferase assay. The luciferase activity in about $10^5$ cells of each clone varied from $10^3$ to $10^6$ RLU, which is 2 to $2 \times 10^3$ times greater than that in untransfected BJAB cells (data not shown). Of the clones identified as having the luciferase gene integrated into the cellular genome, 25% had background luciferase activity of $<10^4$ RLU per $10^5$ cells. Multiple clones with low levels of luciferase activity were characterized to permit detection of transcription that might be activated by EBNA-1. 100% of the clones isolated with background luciferase activity of <10$^4$ RLU per 10$^5$ cells were detectably responsive to EBNA-1 (data not shown).

Figure 2A:
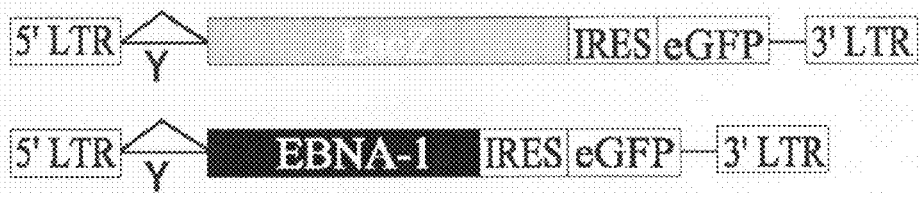
FIG. 2. Transcription of integrated templates induced by EBNA-1 is dose dependent. (A) Structures of retroviral vectors employed to establish EBNA-1's dose-dependent induction of transcription. The control vector expresses β-galactosidase (LacZ), and both it and the vector expressing EBNA-1 also express enhanced GFP (eGFP), whose translation is mediated by an internal ribosomal entry site (IRES). LTR, long terminal repeat. (B) Fluorescence-activated cell sorter profiles reflecting the sorting of infected cells as a function of the level of their expression of eGFP and the level of expression of EBNA-1 as measured by Western blotting in one set of infected, sorted cells 48 hours following infection. (C) Mean RLU obtained in two independent experiments performed in duplicate were normalized by setting the RLU output from cells infected with LacZ virus expressing low GFP to 1. The differences in RLU in cells with integrated FR-TK-luciferase infected with a retrovirus expressing EBNA-1 and sorted for different levels of expression of eGFP are statistically significant ($P<0.05$; Jonckhere-Terpstra test). The error bars indicate standard errors of the means.
Figure 2B:
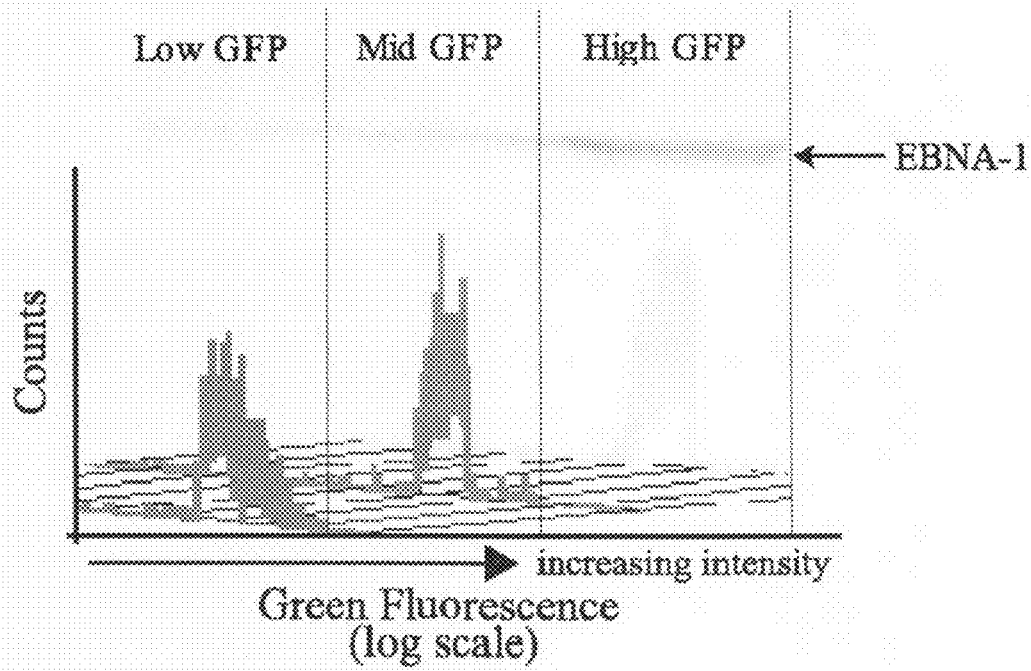
Figure 2C:
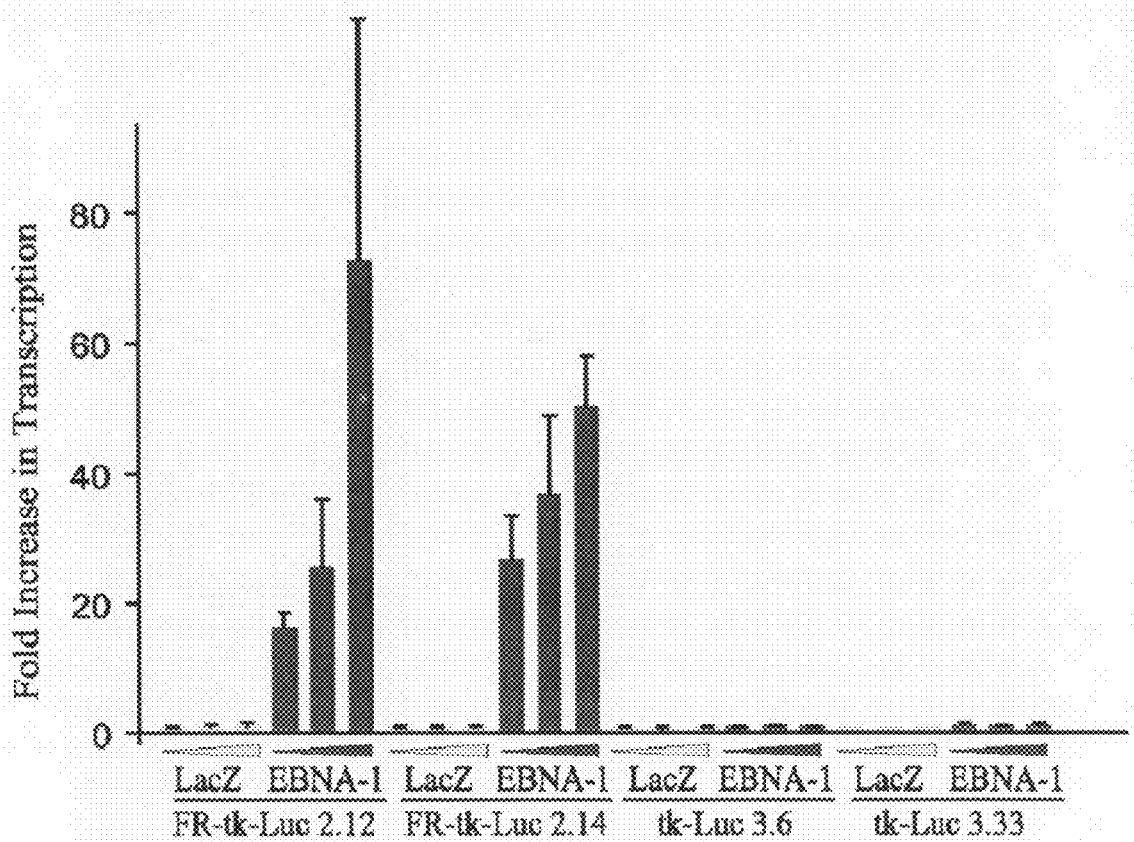

Two BJAB clones stably expressing FR-TK-luciferase and two clones stably expressing TK-luciferase were chosen for further characterization. These cells were infected with retroviral vectors expressing β-galactosidase or EBNA-1 (FIG. 2A). The infected cells were sorted to yield those with the lowest 30%, middle 30%, and highest 30% green signals, which were confirmed to express corresponding levels of EBNA-1 by Western blot analysis (FIG. 2B). EBNA-1 activated transcription dose dependently (P<0.05; Jonckhere-Terpstra test) from those integrated templates with its binding sites in FR present in cis (FIG. 2C).

Figure 3A:
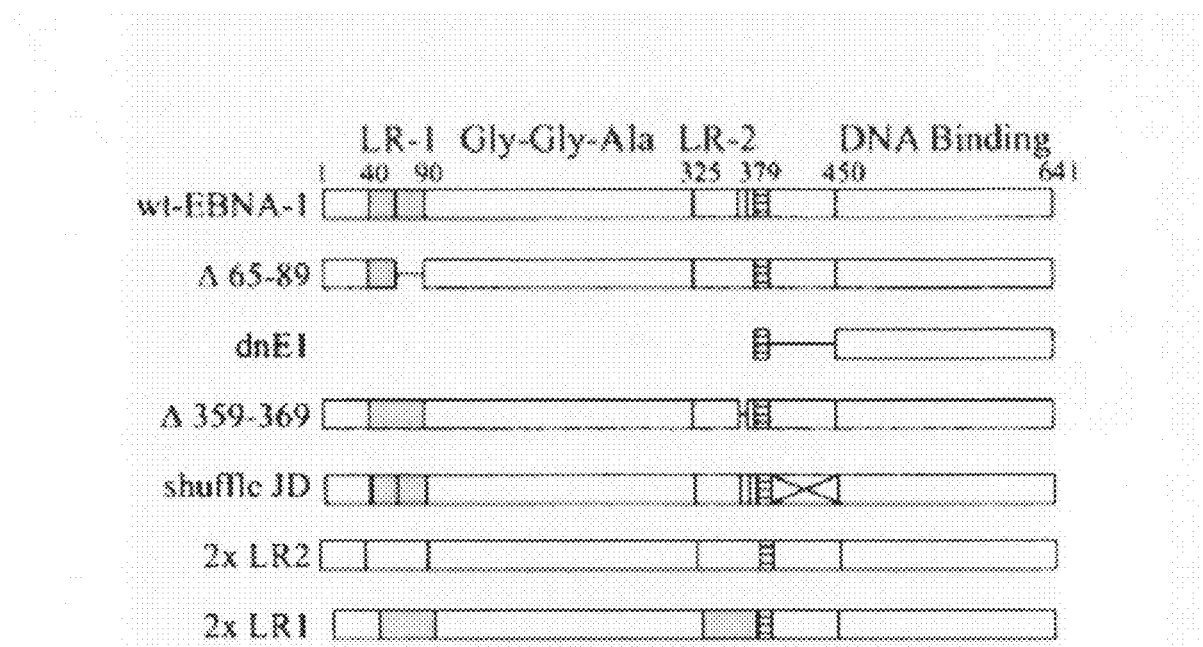
FIG. 3. Mutational analysis of EBNA-1 identifies a transcriptional activation domain within LR1. (A) Derivatives of EBNA-1 are depicted schematically. EBNA-1 has two highly charged regions within its amino terminus, LR1 (shaded boxes) and LR2. The nuclear localization signal of EBNA-1 is found adjacent to a putative flexible linker domain or JD and is represented in all derivatives by the hatched boxes. The Gly-Gly-Ala repeats span about 225 residues in the B95-8 strain of EBV. The derivative used in these studies contains only three Gly-Gly-Ala repeats. wt, wild-type. (B) Western blot analysis demonstrating expression levels of the various derivatives relative to that of wild-type EBNA-1. The membrane was simultaneously probed with antibodies to EBNA-1 and β-actin, which served as a loading control. The relative levels of expression of the transfected derivatives of EBNA-1 were corrected for loading error, and OD units obtained from ImageQuant analysis are represented as OD units per transfected cell at the bottom of each lane. (C) Mean luciferase results corrected for transfection efficiency obtained from at least three independent transfections performed in duplicate are depicted graphically. The increases in transcription over empty vector (mean increase [n-fold] over BJAB cells lacking integrated FR-TK-luciferase, 10; average number of RLU, 5,425±231) mediated by wt-EBNA-1 (mean increase [n-fold] over empty vector, 26 [$P=5.3\times10^{-6}$]; average number of RLU, 85,000±3,780), Δ359-369 (mean increase [n-fold] over empty vector, 21 [$P=0.009$]; average number of RLU, 95,900±17,800), shuffled JD (mean increase [n-fold] over empty vector, 56 [$P=0.05$]; average number of RLU, 116,000±10,700), and 2XLR1 (mean increase [n-fold] over empty vector, 46.7 [$P=0.007$]; average number of RLU, 21,200±31,000) are significant. The apparent increases in transcription over wild-type EBNA-1 mediated by the shuffled JD and 2XLR1 derivatives are not statistically significant ($P>0.05$). The derivatives Δ65-89 (mean increase [n-fold] over empty vector, 1.5 [$P=0.85$]; average number of RLU, 6,510±491), 2XLR2 (mean increase [n-fold] over empty vector, 2.5 [$P=0.21$]; average number of RLU, 9,169±1,070); and dnE1 (mean increase [n-fold] over empty vector, 2.4 [$P=0.33$]; average number of RLU, 8,957±1,800) were found to have no effect on transcription from the integrated template.
Figure 3B:
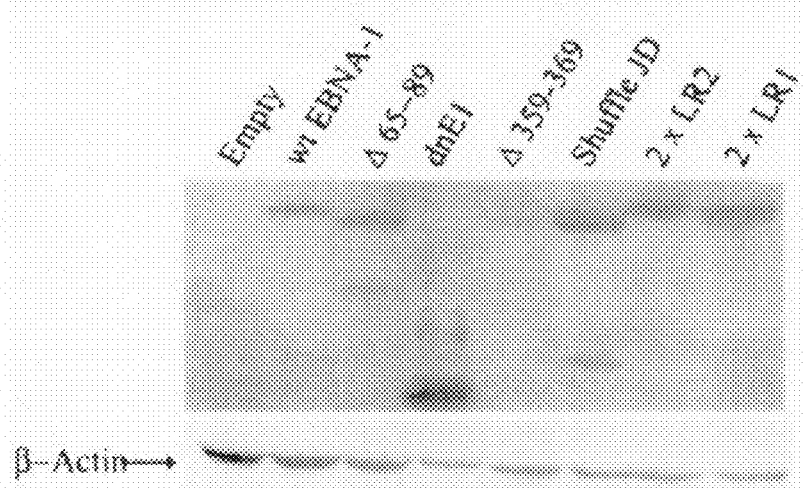
Figure 3C:
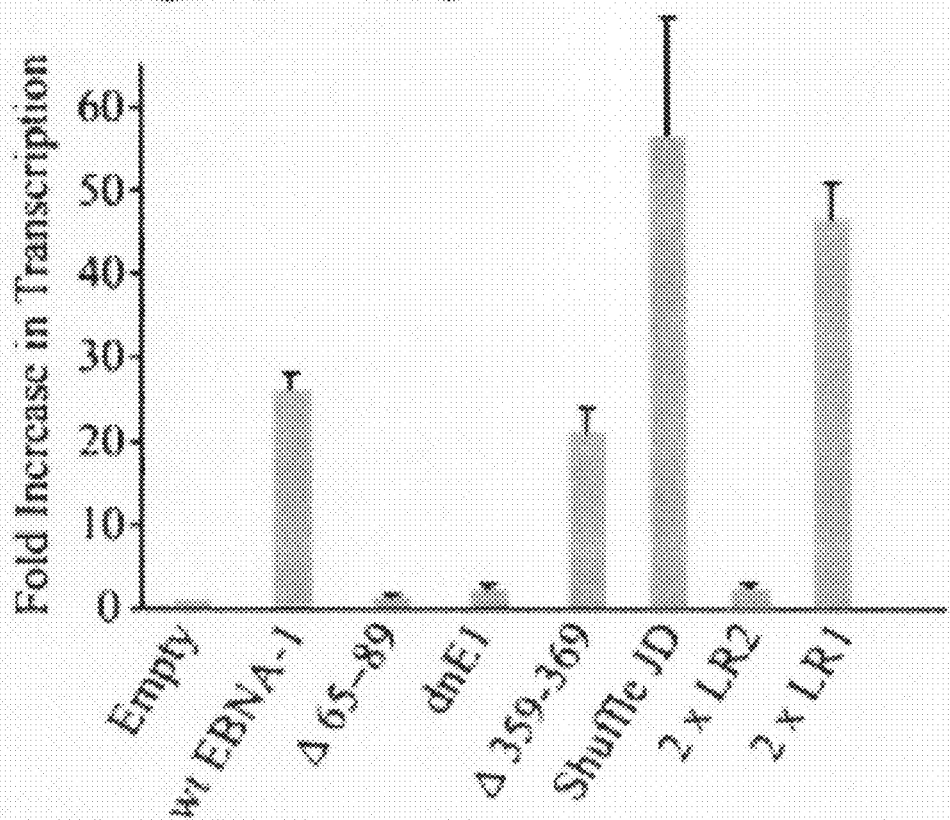

Genetic analysis of EBNA-1 transcriptional activation. Six derivatives of EBNA-1 were analyzed to identify elements within it that could contribute to its transcription of either integrated or newly introduced templates (FIG. 3A). All derivatives were constructed to contain both the EBNA-1 nuclear localization signal and its DNA-binding and dimerization domain to insure that they would have the ability to home to the nucleus and to bind DNAs site specifically. A rabbit antibody to the EBNA-1 DNA-binding and dimerization domain was used in order to detect each of the derivatives with equal efficiency (FIG. 3B). Expression vectors for wild-type EBNA-1 and these six derivatives were introduced into a clone of BJAB cells in which FR-TK-luciferase was integrated, and the levels of luciferase activity were measured (FIG. 3C). Three derivatives (Δ359-369, shuffle JD, and 2XLR1) stimulated luciferase activity to the same level as did wild-type EBNA-1 (P<0.05). These derivatives lack the charged, unique sequences in linking region 2 (LR2), have had the amino acids of the putative JD randomized, and lack all of LR2, respectively. The last derivative, 2XLR1, has LR1 substituted for LR2. LR1 and LR2 are the linking regions of EBNA-1 and have been shown to contribute to the activation of transcription and replication mediated by EBNA-1 (Mackey et al., 1999; Wu et al., 2002). In vitro, the linking regions are essential for linking DNAs to which EBNA-1 binds site specifically (Ceccarelli et al., 1998; Mackey et al., 1995; Mackey et al., 1999; Mackey et al., 1997; Middleton et al., 1992). In vivo, they are essential for tethering EBNA-1 to chromosomes (Marechal et al., 1999).

The derivative shuffled JD activated transcription like wild-type EBNA-1, demonstrating that the EBNA-1 sequence between 379 and 450 is not critical for this function. All of the derivatives that activated transcription as efficiently as did wild-type EBNA-1 had LR1 intact (FIG. 3A). A derivative of EBNA-1 with the unique sequences within LR1 deleted, Δ65-89, lost the ability to promote transcription (FIG. 3C). In fact, both of the derivatives lacking intact LR1 (Δ65-89 and 2XLR2) behaved as did a dominant-negative derivative of EBNA-1 (dnE1), which also lacks LR1, failing to activate transcription from integrated templates (FIG. 3C) significantly over the level of the empty-vector control (increase over empty vector, 2.4-fold; P=0.33). This failure demonstrates that DNA binding by EBNA-1 to a template is not sufficient for transcriptional activation and that the amino terminus is important for activity from an integrated template. The signals measured with dnE1 are statistically the same as with the empty vector, and both are robust enough to ensure that the signals measured with Δ65-89 and 2XLR2 are real but indistinguishable from the negative controls. Importantly, the derivatives dnE1, 2XLR1, and 2XLR2 affected transcription in a second clone of BJAB cells carrying integrated FR-TK-luciferase, as did the clones documented in FIG. 3C with the same rank order of activities (data not shown). This finding confirms that transcription of the integrated FR-TK-luciferase template mediated by the various derivatives of EBNA-1 is independent of integration events. Taken together, these measurements identify LR1 and pinpoint its unique residues, 65 to 89, as being important for EBNA-1's activation of the transcription of integrated templates.

There was no correlation between the levels of expression of the EBNA-1 derivatives and whether they stimulated luciferase activity. Abrogation of transcriptional activity mediated by EBNA-1 could not be attributed to low levels of expression, as five out of the six derivatives studied (Δ65-89, dnE1, shuffled JD, 2XLR2, and 2XLR1) were found to be expressed at higher levels than wild-type (FIG. 3C). The other three derivatives of EBNA-1, Δ65-89, dnE1, and 2XLR2, failed to activate transcription appreciably over the control transfected cells (FIGS. 3B and C). The last derivative studied, Δ359-369, was expressed at levels similar to those of wild-type EBNA-1 and activated transcription from integrated templates as efficiently as did wild-type EBNA-1 (FIGS. 3B and C).

Figure 4A:
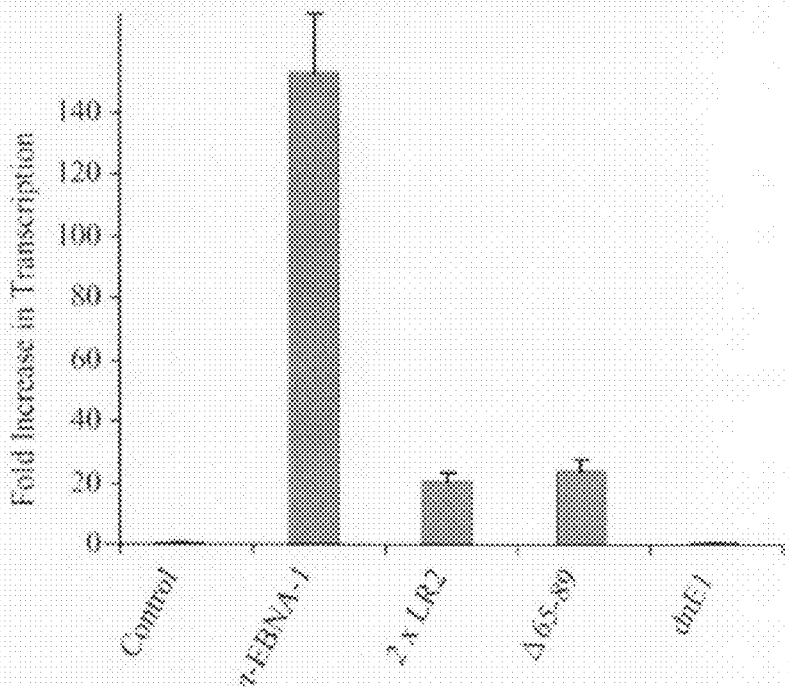
FIG. 4. The ability of EBNA-1 to activate transcription from transfected templates is independent of its ability to activate transcription from integrated templates. (A) The mean CAT activities obtained in three independent experiments performed in duplicate normalized to the CAT activity obtained in cells transfected with FR-TK-CAT and an empty vector control are depicted graphically. The CAT activity obtained from cells transfected with a vector encoding wild-type (wt) EBNA-1 was 150-fold higher than that obtained from cells transfected with a control plasmid ($P=0.002$). The CAT activity obtained from cells transfected with a vector encoding Δ65-89 was 24-fold higher than that obtained from cells transfected with a control plasmid ($P=0.001$). The derivative 2XLR2 was also found to increase transcription from the transfected template 20-fold over cells transfected with a control plasmid ($P=0.002$), while the dnE1 derivative had no effect on transcription from this template ($P=0.3$). (B) The Δ65-89 derivative of EBNA-1 activates transcription from transfected templates in a dose-dependent fashion ($P=0.003$; Jonckhere-Terpstra test). BJAB cells were transfected with 50 ng of a plasmid encoding FR-TK-luciferase with increasing amounts of plasmids encoding either wild-type EBNA-1 or Δ65-89. Luciferase activity was assayed 48 hours posttransfection and is represented on the y axis as induction (n-fold) over cells transfected with a vector encoding FR-TK-luciferase in the absence of EBNA-1. The error bars indicate standard errors of the means.
Figure 4B:
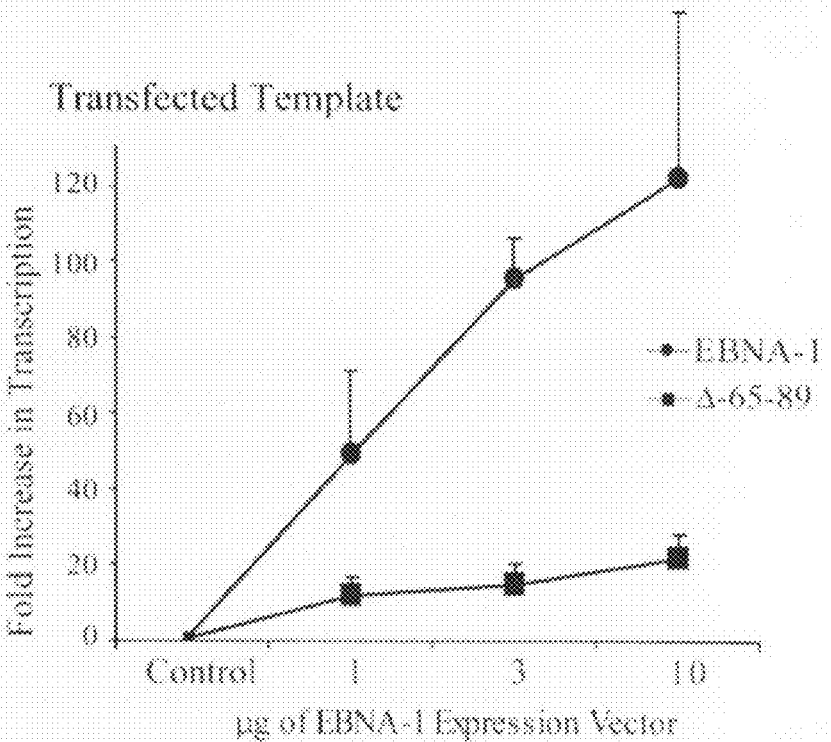

A derivative of EBNA-1 can selectively activate transcription of transfected templates. To determine if the domains within EBNA-1 required to activate transcription of integrated templates were also required to activate the transcription of transfected templates, plasmids encoding EBNA-1 or one of its derivatives were transfected into EBV-negative cells along with a plasmid expressing FR-TK-CAT. The signals from these experiments were normalized to the CAT activity expressed from FR-TK-CAT in the presence of an empty vector rather than to TK-CAT because the latter vector has a higher spontaneous level of activity than does FR-TK-CAT (Reisman et al., 1986; Wysokenski et al., 1989). EBNA-1 lacking all of LR1 (2XLR2) and EBNA-1 lacking only amino acids 65 to 89 failed to activate the transcription of integrated templates (FIG. 3C) but activated the transcription of the transfected template about 10-fold over the control value (FIG. 4A; P=0.009). The dominant-negative derivative, dnE1, failed to activate either template and thus served as a negative control in the experiments. To confirm these observations, BJAB cells were transfected with a plasmid DNA encoding FR-TK-luciferase with increasing amounts of plasmid DNAs encoding either wild-type EBNA-1 or the derivative of EBNA-1 lacking amino acids 65 to 89 (FIG. 4B). The Δ65-89 derivative activated transcription from a transfected template dose dependently (P<0.005; Jonckhere-Terpstra test). EBNA-1 therefore encodes a function that activates the transcription of transfected templates but not of integrated templates.

Figure 5A:
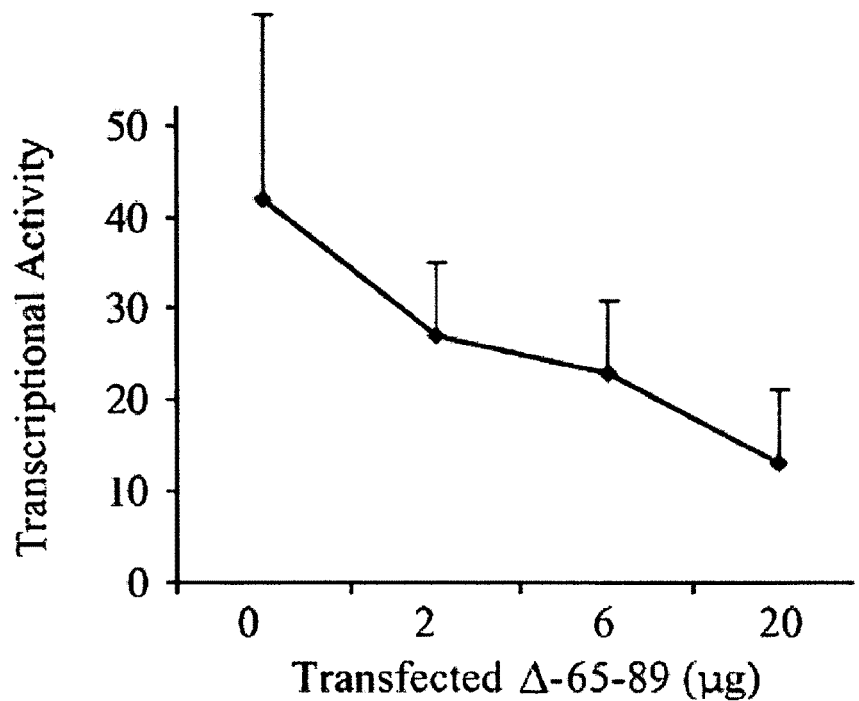
FIG. 5. The derivative of EBNA-1 with amino acids 65 to 89 deleted inhibits wild-type EBNA-1's transcription function in a dominant-negative manner. (A) Graphic representation of the results of three independent experiments performed in duplicate using BJAB cells stably transfected with FR-TK-luciferase plus 2 μg of a vector encoding EBNA-1 and either no vector or increasing amounts of a vector encoding Δ65-89. (B) Graphic representation of the results of three independent experiments performed in duplicate in which BJAB cells were transiently transfected with a plasmid encoding FR-TK-luciferase along with 3 μg of one encoding EBNA-1 and no vector or increasing amounts of the vector encoding Δ65-89. The decrease in luciferase activity mediated by Δ65-89 is statistically significant in both panels ($P\leq0.004$; Jonckhere-Terpstra test). The error bars indicate standard errors of the means.
Figure 5B:
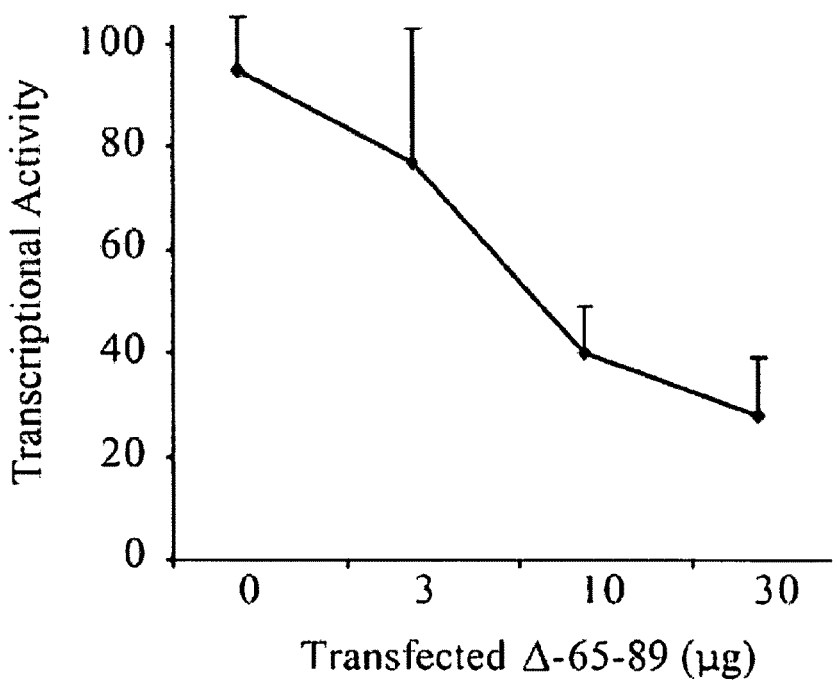

The ability of EBNA-1 to support transcription is inhibited by coexpression of Δ65-89. One derivative of EBNA-1, dnE1, has been well characterized as a dominant-negative mutant of EBNA-1 that inhibits both EBNA-1's activation of transcription and its support of replication, at least in part by competing for wild-type site-specific DNA binding (Kirchmaier et al., 1997). The mutant of EBNA-1 with the deletion of the transcriptional activation domain found within amino acids 65 to 89 may inhibit transcription mediated by EBNA-1. Expression of increasing amounts of the Δ65-89 derivative resulted in significant inhibition of the ability of EBNA-1 to activate transcription from both integrated (FIG. 5A) and transfected (FIG. 5B) templates (P≦0.004; Jonckhere-Terpstra test).

Discussion

Multiple clones of EBV-negative cells were established with EBNA-1-responsive templates integrated into the cellular DNA. The transcription of these integrated templates can be increased by EBNA-1 in all clones isolated with <$10^4$ RLU per $10^5$ cells at baseline (data not shown); the increase in transcription mediated by EBNA-1 in these clones was proportional to the level of expression of EBNA-1 (FIG. 2). Such clones constituted about 25% of those isolated. A recent study also analyzed EBNA-1 activation of transcription from integrated templates but failed to detect it (Kang et al., 2001). That study used uncloned populations of cells in which the high basal levels of reporter expression likely masked the stimulation that EBNA-1 would yield in the responsive cells, thereby limiting the ability to detect transcriptional activity from integrated templates (Kang et al., 2001). The present study of six derivatives of EBNA-1 showed that amino acids 65 to 89 are essential to activate transcription from integrated templates. This domain of EBNA-1 contributed to transcription from transfected templates but was not required for the activation of gene expression from these templates (FIGS. 3 and 4). A derivative of EBNA-1 lacking its first 330 residues, which include LR1 and its Gly-Gly-Ala repeats, also failed to activate transcription from an integrated template (data not shown) but has been found to activate transcription of transfected templates (Kirchmaier et al., 1997). It was further shown that a derivative of EBNA-1 lacking amino acids 65 to 89 inhibits the ability of wild-type EBNA-1 to activate transcription from both integrated and transfected templates (FIG. 5).

The different contributions to transcription of EBNA-1 may play distinct roles in the EBV life cycle. DNAs of herpesviruses are packaged free of nucleosomes in the viral capsid (Cui et al., 2001). Following infection of cells, the viral DNA must enter the nucleus and be packaged into chromatin (Dyson et al., 1985; Leinbach et al., 1980). EBNA-1, therefore, likely affects gene expression both from naked viral DNA, represented by the transfected templates, and from chromatin-embedded viral DNA, represented by the integrated template in the present experiments.

These findings indicate that EBNA-1 contributes to transcription by two genetically separable mechanisms which can be distinguished by using integrated templates or those introduced by transfection. These two templates differ in that the transfected templates enter the cell as naked DNA and need to be shuttled into the nucleus while the integrated templates are present in the nucleus bound as chromatin. Previous studies have found that EBNA-1-responsive templates microinjected into the cytoplasm of cells had a 100-fold increase in transcriptional activity, while those injected into the nucleus had a 5- to 20-fold increase in the presence of EBNA-1 (Langle-Rouault et al., 1998). These results indicate that EBNA-1 apparently contributes to transcription from nuclear templates, but much of its ability to activate transcription might come from its ability to localize plasmids to the nucleus (Langle-Rouault et al., 1998). In the present studies, EBNA-1 activated transcription from transfected templates by up to 120-fold over background (FIGS. 2 and 4). One derivative, dnE1, has both the EBNA-1 nuclear localization sequence and its DNA-binding domain intact but failed to affect the transcription of transfected templates (FIG. 3C). These two domains of EBNA-1 should be sufficient to shuttle FR-positive DNAs into the nucleus. The failure of dnE1 to activate transcription leads to the hypothesis that EBNA-1 contributes to the activation of transcription by modulating the formation of chromatin on naked templates to which it can bind. This hypothesis is supported by recent work by Avolio-Hunter et al. in which EBNA-1 was shown to destabilize nucleosomes in vitro (Avolio-Hunter et al., 2001). The derivative of EBNA-1 lacking amino acids 65 to 89 failed to activate transcription from integrated templates (FIG. 3C) but was able to activate transcription from a transfected template by at least 24-fold (17% of wild-type function) dose dependently (FIGS. 4A and B). A similar mutant of EBNA-1 with a slightly different deletion (residues 61 to 83) increases the transcription of transfected templates by only 1% (Wu et al., 2002). These findings indicate that EBNA-1 contributes to transcription from both transfected and integrated templates but has at least one function that acts only on transfected templates.

Analyses of additional derivatives of EBNA-1 indicate that LR1 is important to activate transcription of integrated templates. The derivative 2XLR2 lacks LR1 and activated transcription on transfected templates better than does dnE1 (FIG. 4A) (Mackey et al., 1999), but is no better than dnE1 in stimulating transcription on integrated templates (FIG. 3C). The LR1 domain of EBNA-1 also clearly contributed to the transcription of transfected templates; a derivative in which LR2 is replaced with LR1 supported transcription of transfected templates at wild-type levels (FIG. 4A) (Mackey et al., 1999). The idea that LR1 contributes to transcription on both integrated and transfected templates is also supported by the deletion of its unique residues, 65 to 89, dominantly inhibiting wild-type EBNA-1 activation of each kind of template (FIG. 5). However, LR2 can also contribute to transcription on transfected templates. A deviation of EBNA-1 in which LR1 is replaced with LR2 stimulates transcription of transfected templates by 20-fold, which is about 13% of wild-type activity (FIG. 4A).

The fact that EBNA-1's contributions to the transcription of transfected or integrated templates can be separated genetically may have an unexpected benefit. Vectors derived from EBNA-1 are being considered for gene therapy in people (Banerjee et al., 1995; Calos, 1996; Cui et al., 2001; Franken et al., 1996; Harada et al., 2000; Phillips et al., 1999; Sclimenti et al., 1998; Stoll et al., 2001; Wohlgemuth et al., 1996). However, EBNA-1 has been found to be associated with an increase risk of tumor development in some strains of transgenic mice (Wilson et al., 1996). This risk has been attributed in part to EBNA-1's transcriptional activation of host genes (Tsimbouri et al., 2002). The Δ65-89 derivative of EBNA-1 supports long-term extrachromosomal replication of oriP plasmids, as does wild-type EBNA-1 (unpublished observations), but likely does not activate the expression of host cell genes. Thus, it may prove to be an ideal partner in human gene therapy using oriP vectors.

EXAMPLE II

Materials and Methods

Cell Culture and Transient Transfection. EBV-negative B cell lines used in these experiments include BJAB (Klein et al., 1974) and DB75 (Ben-Bassat et al., 1977). EBV-positive B cell lines used in these experiments include 721 (Kavathas et al., 1980), Oku1 (Nonkwelo et al., 1997), AG-876 (Pizzo et al., 1978), 11/17-3 (Sugden et al., 1979), Akata (Takada et al., 1991), GG68 (Weigel et al., 1983), and Sav1 (Ruf et al., 1999). The EBV-positive cell lines, RPMI 1788 (CCL-156), Daude (CCL-213), and Namalwa (CRL-1432), are described in the ATCC catalog. DLD1 cells (CCL-221), an EBV-negative colon carcinoma cell line, and SAOS2 (HTB-85), a human osteosarcoma cell line, are available from the ATCC. The VM-10 cell line (Wu et al., 1993; Wu et al., 1994) was kindly provided by A. Levine (Institute for Advanced Studies, Princeton). VM10 cells were grown at 39° C. and apoptosis was induced by a temperature shift to 32° C.

Retroviral Production and Infection. The dominant-negative EBNA-1 (Dom Neg 1) was described (Kirchmaier et al., 1997; Mackey et al., 1999). The derivative of EBNA-1 lacking amino acids 65-89 (Dom Neg 2) inhibits transcription mediated by wild-type EBNA-1, but supports replication of an oriP plasmid with efficiency similar to that of wild-type EBNA-1 (Example I). Retroviruses were produced and purified as described in Example I.

Analyses of Cells. Infected cells were sorted by fluorescence-activated cell sorter (FACS) Vantage or DIVA (Becton Dickinson), and the population of cells expressing the highest levels of GFP (top 50%) was collected. Different numbers (1-240) of cells were directly deposited into multiple wells of 96-well plates containing 200 µl of culture medium with or without irradiated human fibroblast feeder layers. Wells containing surviving and proliferating cells were identified visually at 10-14 days after sorting. The cloning efficiency was determined by using the Poisson distribution where the cloning efficiency=[−1n(number of negative wells)]/number of cells plated per well. γ-irradiated, human fibroblast feeder layers increased the cloning efficiency of AG876 and Oku1 cells 10- to 15-fold but were shown to have no effect on the fraction of cells with decreased survival mediated by Dom Neg 1 or 2.

Apoptosis Assays. To measure apoptosis after cell sorting, cells were collected and stained with Hoechst 33342 and propidium iodide (Sigma); the total number of cells and apoptotic cells were counted on a hemocytometer by fluorescent microscopy. In all cases, 100-200 GFP-positive cells were examined microscopically.

Labeling of DNA strand breaks by terminal deoxynucleotidyltransferase was performed on both DLD1 and Oku1 cells according to the in situ cell death detection kit, TMR red (Roche Molecular Biochemicals, Indianapolis). In all cases, 100-200 green cells were counted and scored for the number of cells TUNEL-positive by using a Zeiss Axiovert 200M.

PCR. The different methods based on PCR have been described (Nanbo et al., 2002). Cellular actin oligonucleotides included forward primer: 5' TCA CCC ACA CTG TGC CCA TCT ACG A 3' (SEQ ID NO:4); reverse primer: 5° CAG CGG AAC CGC TCA TTG CCA ATG G 3' (SEQ ID NO:5); and probe: 5' ATG CCC TCC CCC ATG CCA TCC TGC GT 3' (SEQ ID NO:6).

BALF-5 oligonucleotides included forward primer: 5' CGG AAG CCC TCT GGA CTT C 3' (SEQ ID NO:7); reverse primer: 5' CCC TGT TTA TCC GAT GGA ATG 3' (SEQ ID NO:8); and probe: 5' TGT ACA CGC ACG AGA AAT GCG CC 3' (SEQ ID NO:9).

OriP specific oligonucleotides included forward primer: 5' GGC GCA AGT GTG TGT AAT TTG T 3' (SEQ ID NO:10); reverse primer: 5' GGG COG GCC AAG ATA GG 3' (SEQ ID NO:11); and probe: 5' CTC CAG ATC GCA GCA ATC GCG C 3' (SEQ ID NO:12).

Akata Strain EBER 1 oligonucleotides included AGGACCTACGCTGCCCTAGA (SEQ ID NO:13) and GCTGGTGGTC CGCATGTTTT (SEQ ID NO:14), and Akata Strain EBER 2 oligonucleotides included AGGACAGCCGTTGCCCTAGTGGTTTCG (SEQ ID NO:15) and GTATTCGGCTTGTCCGCTGTTTTT (SEQ ID NO:16).

Western Blot, Southern Blot, and Statistical Analysis. The methods for detecting EBNA-1, LMP 1, and EBV-viral DNA and statistical analysis have been described (Example I; Shimizu et al., 1996). The Wilcoxon rank sum test was used unless otherwise stated.

Results

Inhibition of EBNA-1 Results in Decreased Survival of EBV-Positive Cells. Retroviral vectors expressing a Dom Neg 1, and enhanced GFP (EGFP) expressed from an internal ribosomal entry site (IRES) were used to infect EBV-positive and -negative, normal and tumor B cells. Control retroviruses used the same bicistronic message with EGFP expressed from the IRES but, in place of Dom Neg 1, had either β-galactosidase (LacZ) or a polylinker sequence. Dom Neg 1 has been shown to inhibit two functions of EBNA-1, its support of extrachromosomal replication and of transcription, to 3% of wild-type levels (Kirchmaier et al., 1997). Dom Neg 1's ability to inhibit EBNA-1's functions is primarily dependent on its ability to bind DNA site specifically and competitively displace wild-type EBNA-1 from the DNA (Kirchmaier et al., 1997). Infected cells were identified by their expression of EGFP, sorted by FACS, and tested for survival by colony formation after limiting dilutions. Two EBV-negative and ten EBV-positive cell lines, including seven BL tumor lines, were tested, and survival data are shown in Table 1. When the cell lines 11/17-3, Akata, Daudi, GG67, Namalwa, and SavI were analyzed as a group, the inhibition of EBNA-1 by infection with a retrovirus expressing Dom Neg 1 resulted in a statistically significant decrease in survival compared with cells infected with a control retrovirus (P=0.007, Wilcoxon rank sum test). 721, RPMI 1788, Oku1, and AG876 cells were infected multiple times with a retrovirus expressing Dom Neg 1 and inhibition of EBNA-1 in these cell lines significantly decreased survival (P=0.0004, 0.04, 0.04, and 0.02, respectively).

TABLE 1

| Cell line | Survival, % Dom Neg 1 | Dom Neg 2 | N | EBV status |
|---|---|---|---|---|
| BJAB | 95 ± 5 | 123 ± 11 | 6 | Negative |
| DG75 | 100 | | 1 | Negative |
| 721 | 3 ± 2 | 10 ± 6 | 7* | Positive |
| RPMI 1788 | 33 ± 3 | | 6* | Positive |
| Oku1 | 14 ± 10 | 15 ± 9 | 3* | Positive |
| AG-876 | 51 ± 23 | 42 ± 10 | 6* | Positive |
| 11/17-3 | 10 | | 1 | Positive |
| Akata | 30 | | 1 | Positive |
| Daudi | 45 ± 11 | | 3 | Positive |
| GG68 | 40 ± 7 | | 2 | Positive |
| Namalwa | 34 ± 13 | | 2 | Positive |
| SavI | 30 ± 3 | | 2 | Positive |

Survival of each cell line infected with a control retrovirus was normalized to 100% and it not shown. Survival of cells infected with Dom Neg 1 or 2 was calculated by multiplying, by 100, the cloning efficiency of cells infected with the Dom Neg-expressing virus divided by the cloning efficiency of cells infected with the control virus. The mean survival and SE of the means are shown. N, the number of observations made for each cell line. *Statistical analysis using the Wilcoxon rank sum test reveals P values < 0.05, indicating a significant decrease in survival when these cell lines were infected with retroviruses expressing Dom Neg 1 or 2. The remaining cell lines were grouped according to their EBV status, and statistical analysis revealed a significant decrease (P = 0.007) in survival mediated by infection of these EBV-positive cells with a retrovirus expressing Dom Neg 1.

Whereas EBV DNA is generally maintained extrachromosomally, a few tumor cell lines have their viral DNA integrated into host chromosomes. One such cell line is Namalwa, whose survival was reduced by 50-85% by inhibiting EBNA-1's functions (Table 1). This finding likely indicates that EBNA-1's support of transcription, not just its support of extrachromosomal replication, is important for survival of EBV-positive BL cells. A derivative of EBNA-1 that has been shown to inhibit EBNA-1's ability to activate transcription (Example I), but supports replication of an EBV-derived plasmid at wild-type levels, was used to test whether EBNA-1's activation of transcription likely contributes to survival of EBV-positive BL cells. This derivative, termed Dom Neg 2, was inserted into a retroviral vector and, along with Dom Neg 1, was used to infect one EBV-negative cell line, BJAB, and three EBV-positive cell lines 721, Oku1, and AG876. Cells from the 721 line have been derived by infection of normal B cells in vitro, whereas Oku1 and AG876 cells have been derived from BL tumors. Expression of Dom Neg 2 inhibited survival in all EBV-positive cell lines tested as efficiently as does Dom Neg 1 (Table 1). Remarkably, a significant reduction in survival was seen in Oku1 and AG876 cells, which fail to express LMP1, a viral gene required for proliferation of normal EBV-positive cells ($P<0.05$; Rickinson et al., 1987; Kelly et al., 2002; and unpublished observations). Inhibiting EBNA-1 with a Dom Neg derivative that inhibits transcriptional activation mediated by EBNA-1, inhibits survival of EBV-positive normal and BL cells.

Figure 6A:
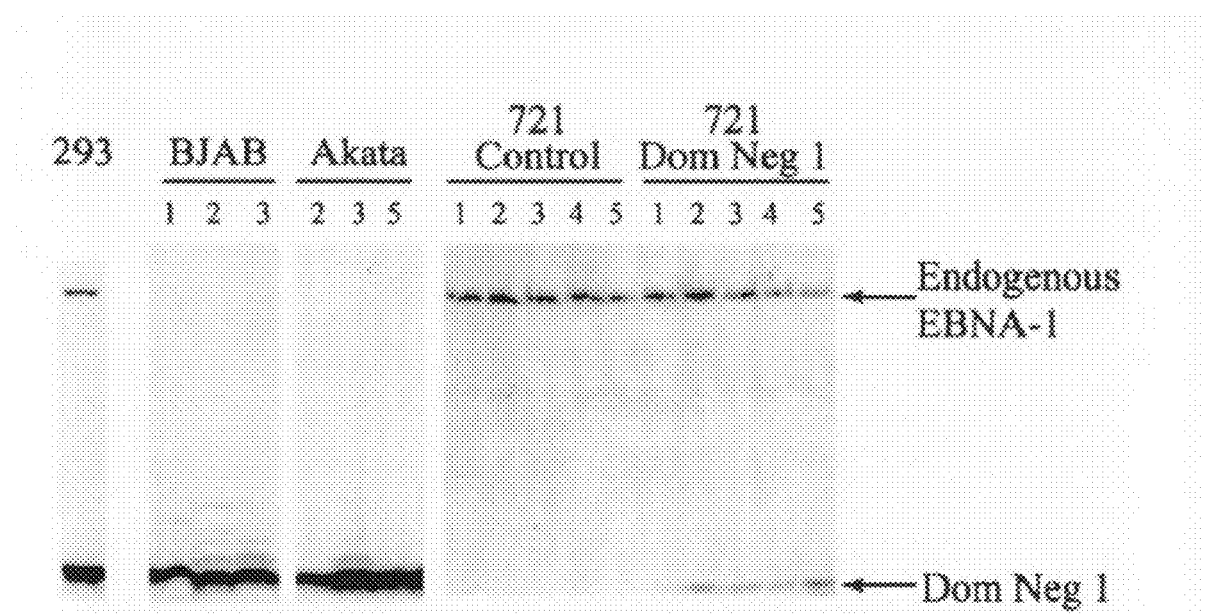
FIG. 6. Inhibition of EBNA-1 by a dominant negative, dnE1, can select for loss of EBV DNA in the EBV-positive Akata cell line. (A) The EBV-negative 293/EBNA-1 and BJAB and the EBV-positive Akata and 721 cell lines were infected with a retrovirus expressing dnE1 (Dom Neg 1). Infected cells were sorted and plated in limiting dilutions. Clones that grew after 14 days were expanded, and Western analyses were performed. Wild-type EBNA-1 is detected in 293/EBNA-1 (293) and 721 cell lines, but not in BJAB cells or in Akata clones 2, 3, and 5. Dom Neg 1 can be detected in all cell lines infected with Dom Neg 1-expressing retrovirus. (B) DNA was harvested from each of the surviving clones, and Southern analyses were performed. EBV DNA readily can be detected in the EBV-positive cell line 721 infected with either the control or Dom Neg 1-expressing retrovirus. However, EBV-DNA has been lost from the Akata clones 2, 3, 5, 6, and 8 that were infected with Dom Neg 1, which correlates with the loss of EBNA-1 expression in clones 2, 3, and 5 (see A above). EBV DNA from the Akata clones infected with control retrovirus was readily detected.
Figure 6B:
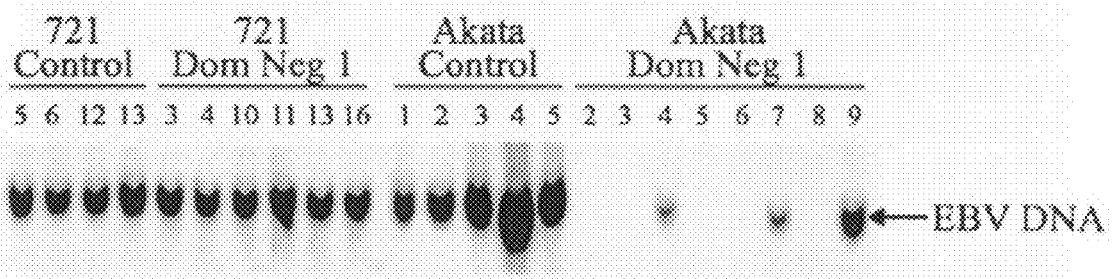
Figure 7A:
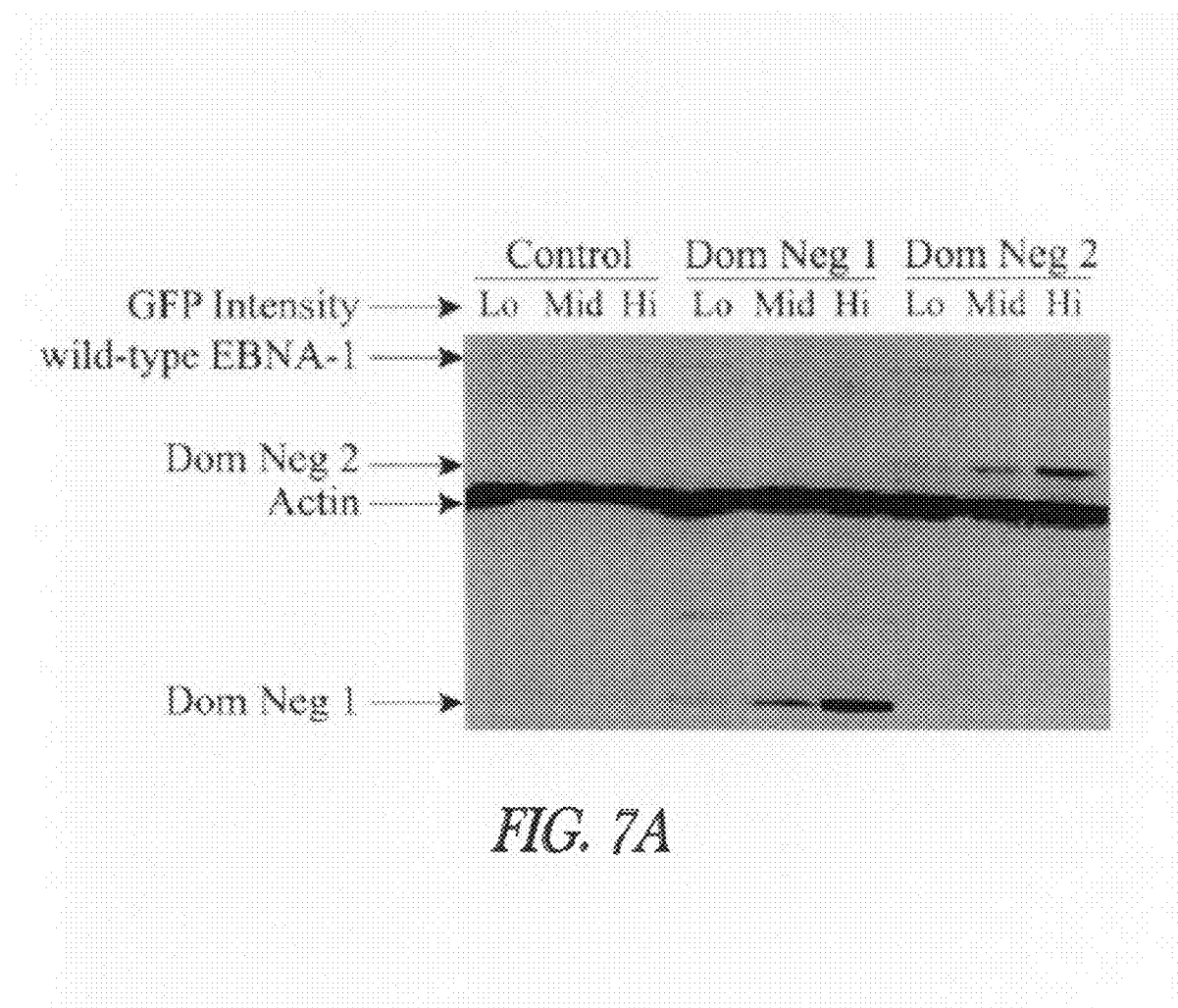
FIG. 7. Inhibition of EBNA-1 leads to a dose-dependent decrease in survival. (A) The EBV-positive, normal B cell line, 721, was infected with the control retrovirus or ones expressing Dom Neg 1 or Dom Neg 2 (EBNA-1 with a deletion of residues 65-89, i.e., Δ65-89). Infected cells were sorted 72 hours postinfection for the top 15%, middle 15%, and bottom 15% of green intensity. The sorted cells were collected, and Western blots were performed. (B) Cells were infected and sorted for the top 15% green, middle 15% green, and bottom 15% of green expression, and were assayed for survival. The decrease in survival between low, middle, and high GFP expression of cells infected with Dom Neg 1 or 2 is statistically significant in all three of the EBV-positive cell lines tested (P<0.05, Jonckhere-Terpstra test).
Figure 7B:
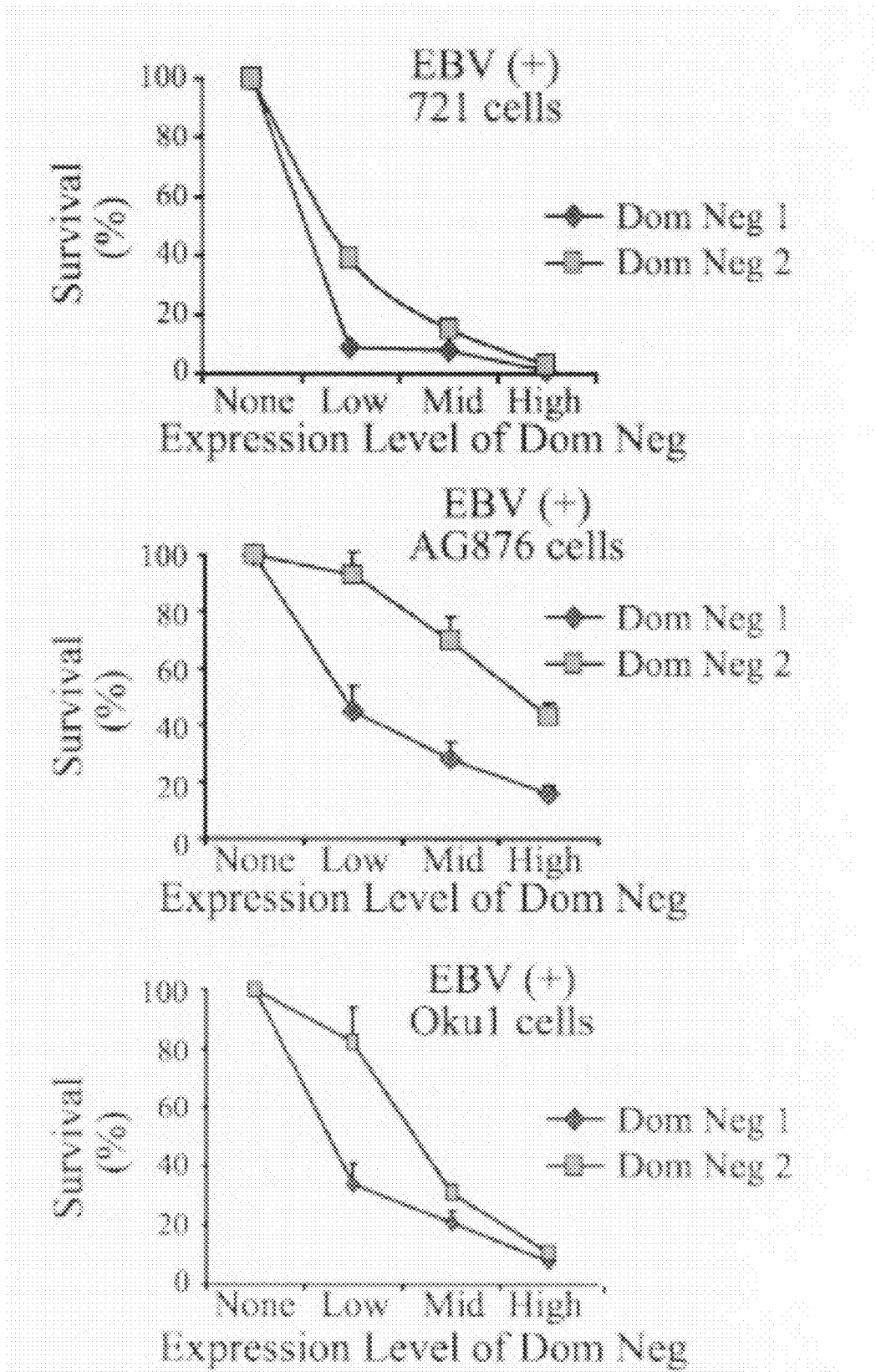

Inhibition of EBNA-1 Decreased Survival of Cells in a Dose-Dependent Manner. In the present experiments, some cells transduced with the Dom Neg derivatives of EBNA-1 survived (Table 1). It was unclear whether their survival reflects differences in the level of expression of the inhibitory genes, or an ability of a subset of EBV-positive cells to survive independent of EBV, as has been demonstrated for atypical BL-derived cells lines such as Akata (Shimizu et al., 1994). Infection of EBV-positive Akata cells with the retrovirus expressing Dom Neg 1 does select survivors that have lost EBV DNA (FIG. 6B). However, 721 cells that survive infection with the retrovirus expressing Dom Neg 1 retained viral DNA and expressed low levels of the inhibitor (FIG. 6). Therefore, it was determined whether cells survive because the level of expression of the Dom Neg 1 or 2 derivatives is insufficient to inhibit EBNA-1's functions. Because the level of expression of Dom Neg 1 and 2 proteins detected in sorted populations corresponded to intensities of EGFP used to sort the populations (FIG. 7), the level of expression of GFP could be used to select cells with different levels of these inhibitors of EBNA-1. EBV-negative BJAB cells and three EBV-positive cell lines, 721, Oku1, and AG876, were infected with the control, Dom Neg 1, or 2 retroviruses. These infected populations of cells were then FACS sorted for those with the top 15%, middle 15%, or bottom 15% intensities of GFP, and the sorted cells were plated in limiting dilutions. The inhibition of survival by both Dom Neg 1 and 2 is dose-dependent in the three EBV positive cell lines tested ($P<0.05$ in all cases, Jonckhere-Terpstra test; FIG. 7B), whereas varying levels of expression of the control virus had no effect on their survival (data not shown). Survival of the EBV-negative BJAB cells was independent of the levels of expression of any of the retroviruses (data not shown). Inhibiting EBNA-1 inhibits survival of EBV-positive normal and tumor cells in a dose-dependent manner, holding promise that the effective inhibition of EBNA-1's functions in patients would kill EBV-positive tumors efficiently.

Figure 8:
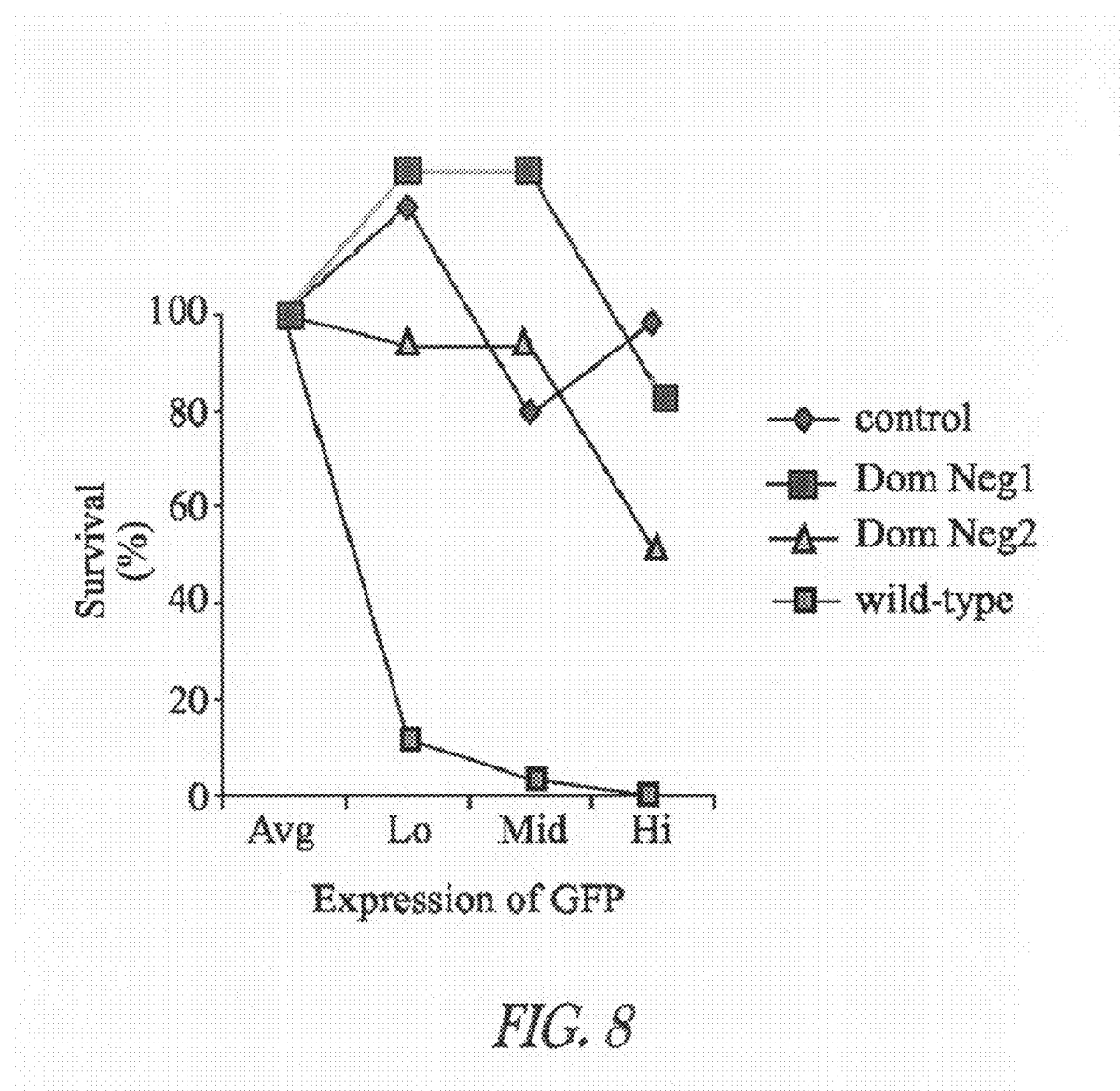
FIG. 8. The Dom Neg derivatives of EBNA-1 do not inhibit growth of EBV-negative B cells, whereas efficient expression of wild-type EBNA-1 does. The EBV-negative B cell line, BJAB, was infected with retroviruses expressing control, Dom Neg 1 or 2, or wild-type EBNA-1. Infected cells were sorted 48 hours postinfection for the highest 15%, middle 15%, and lowest 15% intensity of GFP expression, plated in limiting dilutions, and scored for survival. The average survival of cells infected with the control virus was calculated and was set at 100% survival (average). The survival of cells infected with wild-type EBNA-1 sorted for low, middle, and high was 11%, 3%, and 0.1%, respectively. Survival of cells infected with Dom Neg 1 sorted for low, middle, and high was 129%, 129%, and 86%, respectively. Survival of the cells infected with Dom Neg 2 sorted for low, middle, and high was 93%, 93%, and 51%, respectively.

Dom Neg 1 or 2 Do Not Affect Survival of EBV-Negative Cells as Can EBNA-1. EBNA-1 is the only viral protein consistently expressed in all EBV-associated tumors (Leight et al., 2000). Its protein level of expression in EBV-positive cells appears to be regulated, because the number of molecules of EBNA-1 per cell is not proportional to the viral DNA present in those cells (Sternas et al., 1990). Furthermore, it was found that transient, high-level expression of EBNA-1 in cells can limit their ability to proliferate (FIG. 8). These findings make it essential to test whether the Dom Neg derivatives of EBNA-1 share this phenotype. They do not; for example, when BJAB cells were infected with control, Dom Neg 1-, or 2-expressing retroviruses, sorted 48 hours later for the 15% most, 15% middle, and 15% least green, and plated in limiting dilutions, all survived to proliferate similarly (FIG. 8 and data not shown). However, BJAB cells in parallel experiments infected with a retrovirus expressing wild-type EBNA-1 survived less well than when infected with the other three retroviruses (FIG. 8). Efficient expression of EBNA-1 resulted in the accumulation of large, multinucleated cells, whereas cells infected with either Dom Neg 1 or 2 appeared to be phenotypically normal (data not shown). Therefore, cells infected with a retrovirus expressing wild-type EBNA-1 do not appear to be dying through necrosis or apoptosis; rather, the cells appear to be arrested in mitosis with a disruption in cytokinesis, resulting in the accumulation of large, multinucleated cells. The Dom Neg derivatives of EBNA-1 are not inhibiting survival of EBV-negative cells, as can the efficient expression of wild-type EBNA-1.

Figure 9A:
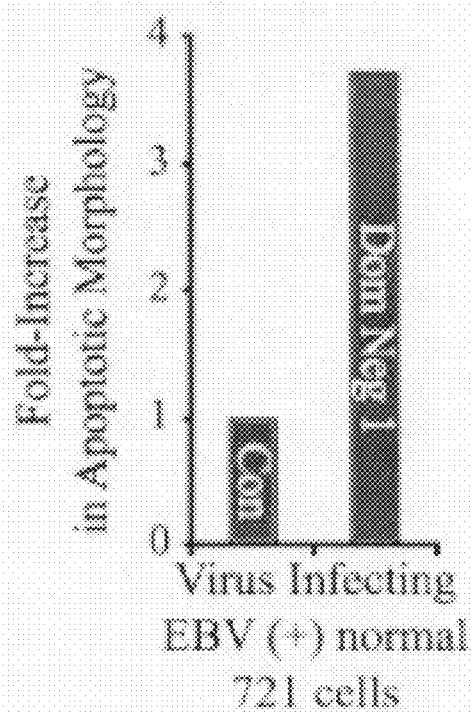
FIG. 9. Inhibition of EBNA-1's functions by Dom Neg 1 or 2 leads to apoptosis of EBV-positive cells without their prior loss of viral DNA or EBERs. (A) The EBV-positive normal B cell line, 721, was infected with retroviruses expressing either control or Dom Neg 1. Morphologic evidence of apoptosis was present in 5-25% of 721 cells infected with Dom Neg 1 in three independent assays, which was 4-fold greater than the evidence of apoptosis identified in cells infected with control virus (P<0.05). (B) Seventy-two hours postinfection, the EBV-positive BL cell line, Oku1, was scored for the fraction of green cells staining positively for apoptosis by the TUNEL assay. In three independent infections, each performed in duplicate, the fraction of cells infected with Dom Neg 1 or 2 that stained positively by the TUNEL assay ranged from 20% to 45%, which was seven to eight times higher than that of cells infected with the control retrovirus (P<0.05). (C) Oku1 cells were infected, and, at 72 hours, were stained with annexin V conjugated to Alexa Fluor® 647. Green cells were sorted plus or minus annexin V, their DNA was isolated, and the number of molecules of EBV DNA was assayed by real-time PCR and normalized to values of actin. The number of EBV DNA molecules does not change significantly in cells that are undergoing apoptosis. (D) Oku1 cells were infected, and cells were sorted 72 hours postinfection for the top 15%, middle 15%, and bottom 15% of green intensity. Reverse transcription followed by PCR was performed on each fraction to determine relative expression levels of the EBER1, EBER2, and actin genes. Below each lane are shown expression levels of each of the bands adjusted for the intensity of the actin amplification product relative to the intensity of the actin product from the uninfected cells. The levels of EBER1 and EBER2 are not related to the survival of the infected Oku1 cells.

Inhibition of EBNA-1 Results in Apoptosis of EBV-Positive Cells. The fate of the EBV-positive cells in which EBNA-1 was inhibited was examined to determine the mechanism by which the cells failed to survive. The survival of EBV-negative BJAB cells and EBV-positive 721, RPMI 1788, AG876, Daudi, and Oku1 cells was assayed by infecting them with control or Dom Neg 1 virus, sorting for infected cells, and monitoring their proliferation in bulk cultures. BJAB cells infected with either virus proliferated similarly, whereas the EBV-positive cells infected with Dom Neg 1 virus grew more slowly than when infected with the control virus (data not shown). EBV-positive cells would be killed were EBV to undergo productive infection in them. Therefore, cells were assayed for the expression of EBV lytic antigens and a background staining was detected in 1.5% and 1.9% in control and Dom Neg 1-virus-infected 721 cells at 3 days postinfection, respectively. This similar background level of staining indicates that the inhibition of EBNA-1 does not induce EBV's lytic cycle. Analysis of the nuclear morphology of these normal, EBV-positive cells was revealing, however; staining them with DNA-specific dye, Hoechst 33342, and propidium iodide for apoptotic bodies showed that cells infected with Dom Neg 1 had a 4-fold increase in apoptosis relative to cells infected with a control virus (FIG. 9A). These initial observations were confirmed by detecting apoptotic cells stained with an antibody to active caspase 9 and by detecting annexin V binding by FACS (data not shown).

Figure 9B:
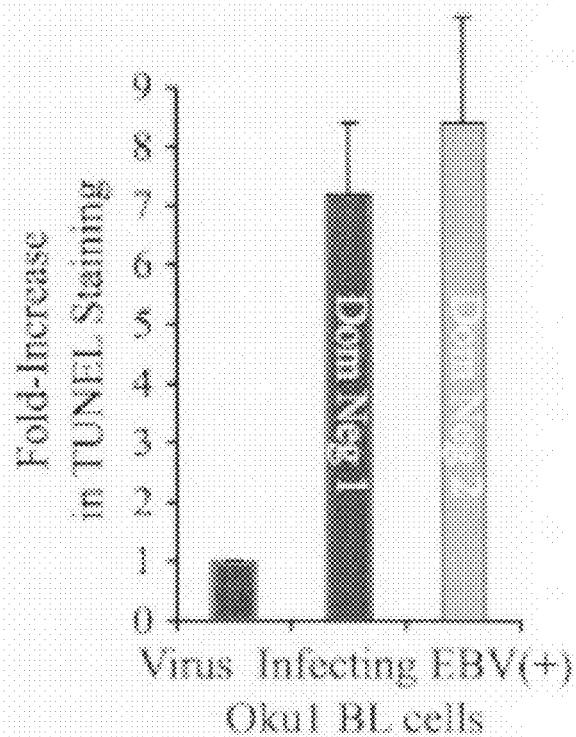

To extend those observations to an EBV-positive BL cell line, Oku1 cells were infected with a control virus or either Dom Neg 1 or 2. Seventy-two hours postinfection, the cells were scored for the presence of apoptosis by terminal deoxynucleotidyltransferase-mediated dUTP nick end labeling (TUNEL) assay. The fraction of cells found positive by the TUNEL assay was increased 7- or 8-fold in cells infected with either Dom Neg 1 or 2 compared with cells infected with control virus (FIG. 9B, $P<0.05$). This apoptosis could result by inhibiting EBNA-1 directly or by EBNA-1's inhibition, leading to loss of viral DNA, and, thereby, other EBV functions. To determine whether loss of the EBV genome contributed to the death of the EBV-positive cells, Oku1 cells were infected with the control retrovirus or a retrovirus encoding Dom Neg 1 or 2. Green, apoptotic cells were identified by staining with annexin V 72 hours postinfection and separated from green, nonapoptotic cells by FACS. DNA from the cell populations was harvested, and the average number of EBV DNA molecules measured per cell by using real-time PCR. The number of viral genomes in those cells undergoing apoptosis resulting from the inhibition of EBNA-1 was similar to that in nonapoptotic cells (FIG. 9C) and unlikely to underlie the observed apoptosis. These cells, therefore, are not dying as a result of loss of the viral genome 72 hours after the inhibition of EBNA-1. This conclusion is consistent with the findings that the level of endogenous EBNA-1 is unchanged in 721 cells infected with high levels of Dom Neg 1 or 2 for 72 hours (FIG. 7A). Inhibiting EBNA-1 in EBV-positive normal and tumor cells inhibited their survival, at least in part, by resulting in apoptosis, whereas loss of the EBV genome is not required for their death.

Figures 9C, 9D:
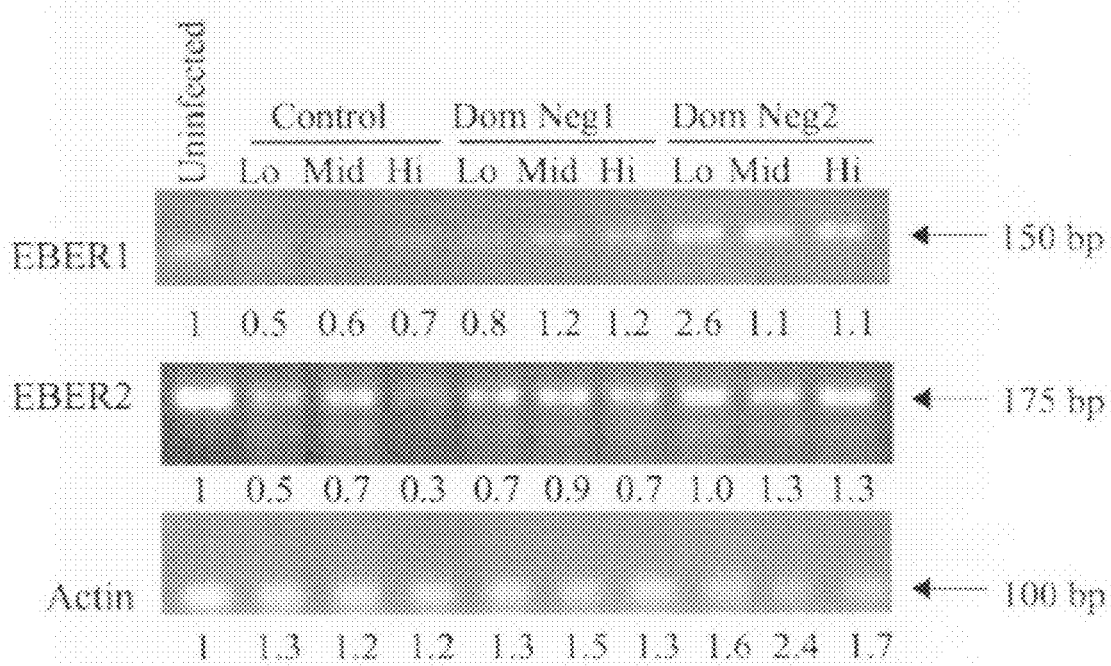

The observation that inhibiting EBNA-1's functions results in apoptosis of EBV-positive cells indicates that EBNA-1 itself directly or indirectly through other EBV genes inhibits apoptosis. Most EBV-positive cells, for example, express two small nonpolyadenylated RNAs, the EBERs, which can affect apoptosis (Nanbo et al., 2002; Komano et al., 1999; Komano et al., 1998; Kitagawa et al., 2000). To determine whether loss of the expression of the EBERs underlies the induction of apoptosis of the EBV-positive BL cell line, Oku1, cells were infected with the control retrovirus or a retrovirus encoding Dom Neg 1 or 2 and sorted 72 hours postinfection for the top 15% green, middle 15% green, and the bottom 15% of green expression. Total RNA was extracted from the cells and reverse transcription, followed by PCR (Nanbo et al., 2002), was performed in a linear range of the assay to determine relative levels of EBER expression (FIG. 9D). Increasing expression of Dom Neg inhibitors of EBNA-1 had no effect on levels of expression of EBERs. Therefore, loss of expression of EBERs cannot explain the 10-fold decrease in survival resulting from the inhibition of EBNA-1 in Oku1 cells (FIG. 7B).

Figure 10A:
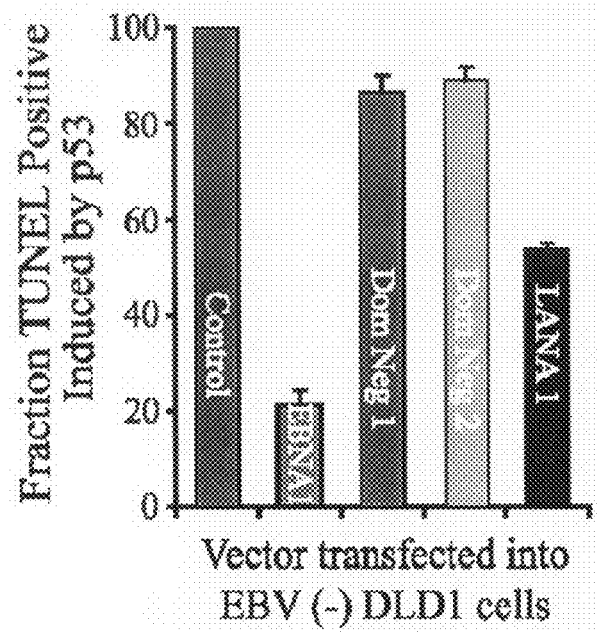
FIG. 10. Expression of EBNA-1 in DLD1 cells inhibits p53's ability to kill cells. (A) The p53-negative human colon carcinoma cell line, DLD1, was transfected with DNA encoding p53 to induce apoptosis in the presence of a DNA-encoding EGFP, and an empty vector (control) or DNAs encoding wild-type EBNA-1, Dom Neg 1 or 2, or LANA-1. Forty-eight hours posttransfection, the cells were stained by the TUNEL assay, and the fraction of TUNEL-positive, green cells was measured in three independent transfections performed in duplicate. EBNA-1 inhibited p53's ability to induce apoptosis 5-fold (P<0.05). Importantly, Dom Neg 1 and 2 had no effect on p53's ability to induce apoptosis. LANA-1 was found to inhibit p53's ability to induce apoptosis by 50%, which was consistent with what has been reported (Friborg et al., 1999). (B) DLD1 cells were transfected with plasmid DNAs expressing EGFP, with or without cells expressing p53 and EBNA-1. Approximately 24 hours posttransfection, cells were trypsinized and plated on gridded tissue culture plates. The number of cells expressing EGFP per grid (low power field) was counted 48 hours and 96 hours posttransfection, and 100-200 cells were counted per plate. There was a statistically significant reduction in the number of cells expressing EGFP and transfected with p53 by 48 hours (15 EGFP-expressing cells per field) compared with control (25 EGFP-expressing cells per field) or EBNA-1 (24 EGFP-expressing cells per field) (P=0.04). This reduction was also seen at 96 hours posttransfection (P=0.02). Fewer green cells transfected with p53 and EBNA-1 (15 EGFP-expressing cells per field) were found when compared with the control (P=0.08) at 48 hours by 96 hours, EBNA-1, when coexpressed with p53, increased the number of green cells per field (15 EGFP-expressing cells per field) compared with cells transfected with p53 alone (seven EGFP-expressing cells per field) (P=0.02). At 96 hours, there is no statistically significant difference in the number of green cells, transfected with GFP from those transfected with GFP plus EBNA-1 (P=0.5), indicating that under these experimental conditions in which EBNA-1 inhibits apoptosis, EBNA-1 alone is not inhibiting survival or proliferation of DLD1 cells.
Figure 10B:
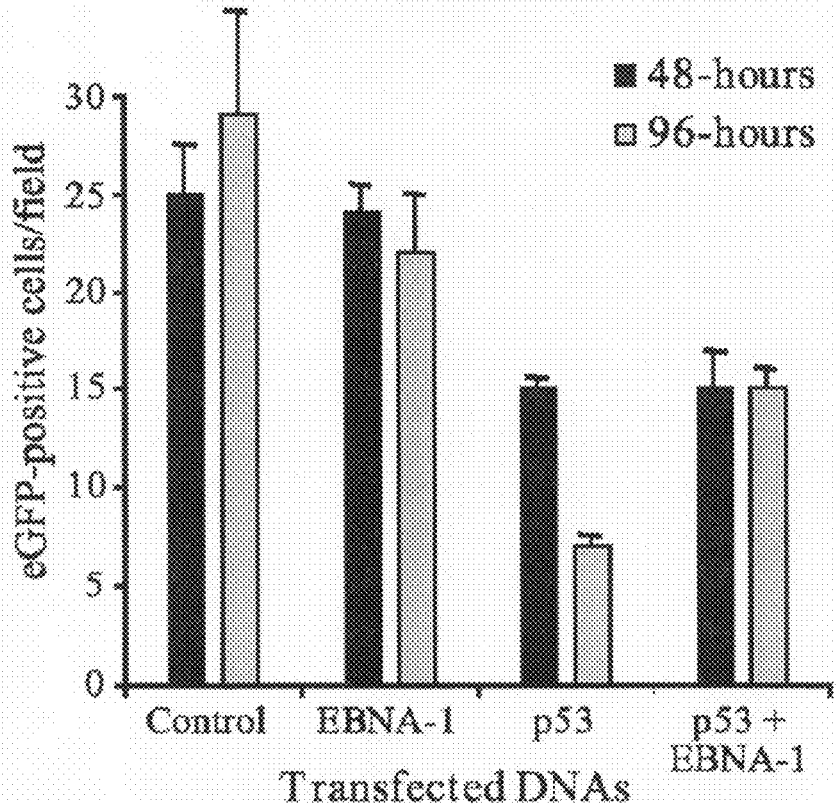

EBNA-1 Can Inhibit Apoptosis in the Absence of the Viral Genome. Apoptosis was induced by efficient expression of p53 in two p53-negative cell lines, SAOS2 and DLD1, as well as in VM10 cells in the presence or absence of transfected EBNA-1. EBNA-1 reduced the number of TUNEL-positive cells by 80% in the DLD 1 cell line (FIG. 10A, P<0.05). Importantly, both Dom Neg 1 and 2 failed to inhibit apoptosis (FIG. 10A). The apoptosis induced by transfection of a p53-expressing vector in SAOS2 cells, and by temperature shift in VM10 cells, which carry a ts-allele of p53 (Wu et al., 1993; Wu et al., 1994), was inhibited by about 50% by expression of EBNA-1 (data not shown). An analogue of EBNA-1, LANA-1, encoded by ORF73 of Kaposi's sarcoma herpes virus (Rainbow et al., 1997), has been found to inhibit p53-mediated apoptosis and served as a positive control in these assays (Friborg et al., 1999). Furthermore, it was demonstrated that expression of EBNA-1 in the presence of p53 leads to a statistically significant increased survival of transfected cells up to 96 hours posttransfection (FIG. 10B), indicating that the diminution of TUNEL-positive cells is not a result of EBNA-1's inhibiting their survival. EBNA-1 in the absence of other EBV genes can inhibit apoptosis. Most EBV-positive BL cells are functionally p53-negative (Farrell et al., 1991); therefore, EBNA-1's ability to inhibit apoptosis is not limited to the inhibition of p53, whereas LANA-1 inhibits p53 directly, and, thus, inhibits only p53-dependent apoptosis (Friborg et al., 1999).

Discussion

That EBV, and EBNA-1 in particular, can inhibit apoptosis in B cells likely contributes to the persistence of EBV-infected cells in vivo. EBV can infect and induce B cells to proliferate during most stages of their development, including pro-B, preB, immature, and mature B cells (Nilsson, 1992). It appears that the majority of the B cells progressing through these stages of development die through apoptosis (Defrance et al., 2002; FIG. 11). Infection of these cells with EBV would require EBV to inhibit apoptosis for infected cells to persist in vivo. A striking example of EBV's potentially rescuing such cells from apoptosis is the identification of Hodgkin and Reed-Sternberg cells, which have nonfunctional rearrangements of their Ig loci but survive in the presence of EBV infection (Kuppers et al., 1997). EBV infection also can drive the expansion of a large fraction of peripheral B cells (Robinson et al., 1980) and be maintained in memory B cells (Kuppers et al., 1997; Babcock et al., 1998), cases again in which EBNA-1's inhibition of apoptosis would allow EBV to persist in vivo. In addition to EBNA-1's inhibiting apoptosis in infected cells, LMP 1, another viral gene usually expressed in EBV-infected B cell, has been thought to inhibit apoptosis. Recent findings with conditional mutants, however, indicate that LMP1's functioning drives proliferation of B cells, whereas its absence leads to quiescence but not to apoptotic death (U. Dirmeier, B. S., and W. Hammerschmidt, unpublished findings). Additionally, when the EBV-positive, normal B cell line 721 was infected with Dom Neg 1 and 2, the expression of LMP1 was found to be independent of their survival (data not shown). Thus EBNA-1's ability to block apoptosis likely allows EBV to persist in vivo and is a survival factor for BL.

Others have used the conditional expression of a Dom Neg derivative of EBNA-1 in one cell line in which EBV DNA is integrated (IB4) and failed to detect an effect of expression of the Dom Neg EBNA-1 on cell survival (Kang et al., 2001). The use of a retrovirus to deliver Dom Neg derivatives to multiple cell lines allowed us to detect a decrease in survival mediated by the inhibition of EBNA-1's functions. The present findings indicate that EBV is required to sustain BLs long after they have evolved to accumulate cellular mutations that render them independent of normal cellular controls. EBV shares this characteristic with human papillomaviruses that cause cervical carcinomas (Goodwin et al., 2000; Goodwin and DiMaio, 2001). Tumors caused by these two human tumor viruses should be treatable by specific antiviral therapies. For EBV-associated BL and, perhaps, for other EBV-associated malignancies, targeting EBNA-1 successfully should provide a potent therapy for these human cancers.

REFERENCES

Aher et al., *Science,* 255:1573 (1992).
Almquist et al., *J. Med. Chem.,* 23:1392 (1980).
Avolio-Hunter et al., *Nucleic Acids Res.,* 29:3520 (2001).
Babcock et al., *Immunity,* 9:395 (1998).
Banerjee et al., *Nat. Med.,* 1:1303 (2001).
Bavaay and Merrifield, "The Peptides," eds. E. Gross and F. Meienhofer, Vol. 2 (Academic Press, 1980) pp. 3-285.
Ben-Bassat et al., *Int. J. Cancer,* 19:27 (1977).
Boxer et al., *Oncogene,* 20:5595 (2001).
Calos, *Trends Genet.,* 12:463 (1996).
Ceccarelli et al., *Gene Ther. Mol. Biol.,* 3:1 (1998).
Clark-Lewis et al., *Meth. Enzymol.,* 287, 233 (1997).
Cui et al., *Gene Ther.* 8:1508 (2001).
Curiel et al., *Proc. Natl. Acad. Sci. USA,* 88:8850 (1991).
Dayhoff, M. O., in Atlas of Protein Sequence and Structure, 1972, volume 5, National Biomedical Research Foundation, pp. 101-110, and Supplement 2 to this volume, pp. 1-10.
Defrance et al., *Adv. Cancer Res.,* 86:195 (2002).
Dubensky et al., *Proc. Natl. Acad. Sci. U.S.A.,* 81:7529 (1984).

Dyson et al., *J. Gen. Virol.*, 66:1931 (1985).
Evens et al., *Curr. Treat. Options Oncol.*, 3:291 (2002).
Evens et al., *Gene Ther.*, 4:264 (1997).
Farrell et al., *EMBO J.*, 10:2879 (1991).
Felgner et al., *Nature*, 337:387 (1989).
Franken et al., *Nat. Med.*, 2:1379 (1996).
Friborg et al., *Nature*, 402:889 (1999).
Gahn et al., *J. Virol.*, 69:2633 (1995).
Goodwin et al., *Cell Growth Differ.*, 12:525 (2001).
Goodwin et al., *Proc. Natl. Acad. Sci. USA*, 97:10978 (2000).
Hann, *J. Chem. Soc.* Perkin Trans I, 307-314 (1982).
Harada et al., *Cancer Gene Ther.*, 7:27 (2000).
Henning et al., *Cell*, 82:555 (1995).
Hirai et al., *Biochem. Biophys. Res. Commun.*, 241:112 (1997).
Holladay et al., *Tetrahedron Lett.*, 24:4401 (1983).
Hruby, *Life Sci.*, 31:189 (1982).
Hudson et al., *Int. J. Pent. Prot. Res.*, 14:177 (1979).
Jennings-White et al., *Tetrahedron Lett.*, 23:2533 (1982).
Kaneda, *Mol. Urol.* 5:85 (2001).
Kang et al., *Proc. Natl. Acad. Sci. USA*, 98:15233 (2001).
Kavathas et al., *Proc. Natl. Acad. Sci. USA.*, 77:4251 (1980).
Kaykas et al., *EMBO J.*, 20:2641 (2001).
Kelly et al., *Nat. Med.*, 8:1098 (2002).
Kennedy and Sudgen, Chapter 3.2 in *Gene Transfer and Expression in Mammalian cells* Elsener Science B. V. (2003)
Kennedy et al., *Mol. Cell. Biol.*, 23:6901 (2003).
Kirchmaier et al., *J. Virol.*, 69:1280 (1995).
Kirchmaier et al., *J. Virol.*, 71:1766 (1997).
Kirchmaier and Sudgen, *J. Virol.*, 72: 4657 (1998)
Kitagawa et al., *EMBO J.*, 19:6742 (2000).
Klein et al., *Proc. Natl. Acad. Sci. USA*, 71:3283 (1974).
Komano et al., *J. Virol.*, 72:9150 (1998).
Komano et al., *J. Virol.*, 73:9827 (1999).
Kuppers et al., *Blood*, 89:1288 (1997).
Langle-Rouault et al., *J. Virol.*, 72:6181 (1998).
Lee et al., *J. Virol.*, 73:2974 (1999).
Lei et al., *Gene Ther.*, 3:427 (1996).
Leight et al., *Rev. Med. Virol.*, 10:83 (2000).
Legerski et al., *Nature*, 360:610 (1992).
Leinbach et al., *J. Gen. Virol.*, 51:45 (1980).
Levitskaya et al., *Proc. Natl. Acad. Sci. U.S.A.*, 94:12616 (1997).
Lindstrom et al., *Oncogene*, 20:2171 (2001).
Lindstrom et al., *Semin. Cancer Biol.*, 12:381 (2002).
Mackey et al., *J. Biol. Chem.*, 272:29873 (1997).
Mackey et al., *J. Virol.*, 69:6199 (1995).
Mackey et al., *Mol. Cell. Biol.*, 19:3349 (1999).
Mackey et al., *Mol. Cell. Biol.*, 19:3349 (1999).
Marechal et al., *J. Virol.*, 73:4385 (1999).
Mautner et al., *Oncogene*, 12:1299 (1996).
Meienhofer in "Hormonal Proteins and Peptides," ed.; C. H. Li, Vol. 2 (Academic Press, 1973), pp. 48-267.
Merrifield, *J. Am. Chem. Soc.*, 85 2149 (1963).
Middleton et al., *J. Virol.*, 66:489 (1992).
Mitchel et al., *J. Virol.*, 69:2968 (1995).
Moran et al., *Cell*, 87:917 (1996).
Morley, *Trends Pharm. Sci.*, pp. 463-468 (1980).
Nanbo et al., *EMBO J.*, 21:954 (2002).
Natarajan et al., *Mol. Cell*, 4:657 (1999).
Needleman and Wunsch, *J. Mol. Biol.* 48: 443 (1970).
Neely et al., *Mol. Cell. Biol.*, 22:1615 (2002).
Niedobitek et al., *Int. J. Exp. Pathol.*, 82:149 (2001).
Nilsson, Hum. *Cell.*, 5:25 (1992).
Nnkwelo et al., *J. Virol.*, 71:6887 (1997).
Ory et al., *Proc. Natl. Acad. Sci. USA*, 93:11400 (1996).
Pearson and Lipman, *Proc. Natl. Acad. Sci. (U.S.A.)* 85: 2444 (1988).
Perales et al., *Proc. Natl. Acad. Sci. U.S.A.*, 91:4086 (1994).
Peterson et al., *Gene*, 107:279 (1991).
Phillips et al., *Plasmid*, 41:198 (1999).
Pizzo et al., *Nature*, 272:629 (1978).
Rainbow et al., *J. Virol.*, 71:5915 (1997).
Reisman et al., *Mol. Cell. Biol.*, 6:3838 (1986).
Rickinson et al., *J. Virol.*, 61:1310 (1987).
Robinson et al., *Nature*, 287:334 (1980).
Rowe et al., *EMBO J.*, 6:2743 (1987).
Ruf et al., *Mol. Cell. Biol.*, 19:1651 (1999).
Sambrook et al., *Molecular Cloning: A Laboratory Manual*, Cold Spring Harbor Laboratory Press (2d ed., 1989)
Satoh et al., *Biochem. Biophys. Res. Commun.*, 238:795 (1997).
Sclimenti et al., *Curr. Opin. Biotechnol.*, 9:476 (1998).
Schmidt et al; *Nat. Med.*, 9:463 (2003).
Shimizu et al., *J. Virol.*, 68:6069 (1994).
Shimizu et al., *J. Virol.*, 70:7260 (1996).
Simmons et al., *Science*, 276, 276 (1997).
Simpson et al., *Mol. Cell Biol.*, 16:5117 (1996).
Smith and Waterman, *Adv. Appl. Math.*, 2: 482 (1981).
Smith et al., *J. Biol. Chem.*, 272:27493 (1997).
Spatola et al., *Life Sci.*, 38:1243 (1986).
Spatola, A. F. in "Chemistry and Biochemistry of Amino Acids, Peptides, and Proteins," B. Weinstein, eds. Marcel Dekker, N.Y., P. 267 (1983).
Spatola, A. F., Vega Data (March 1983), Vol. 1, Issue 3, "Peptide Backbone Modifications" (general review).
Stanfield-Oakley et al., *J. Mol. Biol.*, 256:503 (1996).
Steinitz et al., *Proc. Natl. Acad. Sci. USA*, 72:3518 (1975).
Sternas et al., *J. Virol.*, 64:2407 (1990).
Stewart et al., *Solid Phase Peptide Synthesis*, W. H. Freeman Co., San Francisco (1969).
Stoll et al., *Mol. Ther.*, 4:122 (2001).
Sugden et al., *J. Virol.*, 31:590 (1979).
Sugden et al., *J. Virol.*, 63:2644 (1989).
Szelke et al., European Appln. EP 45665 (1982) 97:39405 (1982).
Takada et al., *Virus Genes*, 5:147 (1991).
Tsimbouri et al., *Oncogene*, 21:5182 (2002).
Unverzagt et al., *J. Am. Chem. Soc.*, 112:9308 (1990).
Utley et al., *EMBO J.*, 13:6031 (1994).
W, X. & Levine, A. J., *Proc. Natl. Acad. Sci. USA*, 91:3602 (1994).
Wallberg et al., *Mol. Cell. Biol.*, 20:2004 (2000).
Weigel et al., *Virology*, 125:287 (1983).
Westphal et al., *Hum. Gene Ther.*, 9:1863 (1998).
Wilson et al., *EMBO J.*, 15:3117 (1996).
Wolff et al., *Science,* 1465 (1990)
Wolgemuth et al., *Gene Ther.*, 3:503 (1996).
Wu et al., *Genes Dev.*, 7:1126 (1993).
Wu et al., *J. Virol.*, 76:2480 (2002).
Wysokenski et al., *J. Virol.* 63:2657 (1989).
Yang et al., *Proc. Natl. Acad. Sci. U.S.A.*, 91:4407 (1993).
Yates et al., *Proc. Natl. Acad. Sci. U.S.A.*, 81:3806 (1984).

All publications, patents and patent applications referred to are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A recombinant vector comprising a DNA segment which encodes a recombinant protein that has the following sequences: an amino acid sequence with at least 90% amino acid sequence identity to residue 1 to residue 40 of a wild-type EBNA-1 protein of Epstein-Barr virus (EBV) having SEQ ID NO:1 which is N-terminal to at least three consecutive tripeptides selected from any combination of the following tripeptides Gly-Gly-Ala, Gly-Ala-Gly, Gly-Gly-Gly, Ala-Gly-Ala, or Ala-Gly-Gly, which are N-terminal to an amino acid sequence with at least 90% amino acid sequence identity to residues 328 to 641 of SEQ ID NO:1, wherein the recombinant protein lacks residues 65 to 89 of the wild-type EBNA-1 protein, wherein the recombinant protein binds an oriP of EBV with an affinity that is at least 10% that of the binding of the wild-type EBNA-1 protein, is noncytotoxic and activates transcription at levels at least 5% that of the wild-type EBNA-1 protein from an extrachromosomal template having an oriP of EBV which is capable of binding the wild-type EBNA-1 protein.

2. The recombinant vector of claim 1 wherein the DNA segment comprises a first DNA fragment encoding residues 1 to 40 of the wild-type EBNA-1 protein and a second DNA fragment encoding residues from residue 328 to the C-terminal residue of the wild-type EBNA-1 protein.

3. The recombinant vector of claim 2 wherein the DNA segment further comprises a third DNA fragment inserted between the first and second DNA fragments, which third DNA fragment comprises a portion of an open reading frame.

4. The recombinant vector of claim 3 wherein the third DNA fragment encodes LR2 of the wild-type EBNA-1 protein.

5. The recombinant vector of claim 1 further comprising the DNA sequence having oriP of EBV.

6. The recombinant vector of claim 5 further comprising a heterologous open reading frame.

7. The recombinant vector of claim 6 wherein the heterologous open reading frame is operably linked to a transcriptional regulatory element.

8. The recombinant vector of claim 7 wherein the transcriptional regulatory element is a promoter.

9. The recombinant vector of claim 7 wherein the transcriptional regulatory element includes an enhancer.

10. The recombinant vector of claim 6 wherein the heterologous open reading frame encodes a therapeutic or prophylactic gene product.

11. The recombinant vector of claim 1 or 10 further comprising a selectable gene or a marker gene.

12. The recombinant vector of claim 1 which encodes a recombinant protein with at least 95% amino acid sequence identity to residues 1 to 40 and to residues 328 to 641 of SEQ ID NO:1.

13. The recombinant vector of claim 1 which comprises the Gly-Gly-Ala repeat region of the wild-type EBNA-1 protein.

14. The recombinant vector of claim 1 wherein the recombinant protein activates transcription from the extrachromosomal template at levels at least 10% that of the wild-type EBNA-1 protein.

15. The recombinant vector of claim 1 which is a plasmid.

16. The recombinant vector of claim 1 which is a recombinant virus.

17. The recombinant vector of claim 1 wherein the amino acid sequence with at least 90% amino acid sequence identity to residues 328 to 641 of SEQ ID NO:1 has a wild-type EBNA-1 nuclear localization sequence.

18. A derivative encoded by the recombinant vector of claim 1.

19. A method to maintain and express a heterologous open reading frame in a cell, comprising contacting a cell with a recombinant plasmid comprising the heterologous open reading frame and a DNA sequence which is capable of binding a wild-type EBNA-1 protein with an affinity that is at least 10% that of an oriP of EBV, which cell expresses a DNA segment which encodes a recombinant protein, wherein the recombinant protein has the following sequences: an amino acid sequence with at least 90% amino acid sequence identity to residue 1 to residue 40 of a wild-type EBNA-1 protein of EBV having SEQ ID NO:1 which is N-terminal to at least three consecutive tripeptides selected from any combination of the following tripeptides Gly-Gly-Ala, Gly-Ala-Gly, Gly-Gly-Gly, Ala-Gly-Ala, or Ala-Gly-Gly, which are N-terminal to an amino acid sequence with at least 90% amino acid sequence identity to residues 328 to 641 of SEQ ID NO:1, wherein the recombinant protein lacks residues 65 to 89 of the wild-type EBNA-1 protein, wherein the recombinant protein binds an oriP of EBV with an affinity that is at least 10% that of the binding of the wild-type EBNA-1 protein, is noncytotoxic, and activates transcription at levels at least 5% that of the wild-type EBNA-1 protein from an extrachromosomal template having an oriP of EBV which is capable of binding the wild-type EBNA-1 protein.

20. A method to maintain and express a heterologous open reading frame in a cell, comprising contacting a cell with a recombinant plasmid comprising the heterologous open reading frame and a DNA sequence which is capable of binding a wild-type EBNA-1 protein with an affinity that is at least 10% that of an oriP of EBV, and a DNA segment which encodes a recombinant protein, wherein the recombinant protein has the following sequences: an amino acid sequence with at least 90% amino acid sequence identity to residue 1 to residue 40 of a wild-type EBNA-1 protein of EBV having SEQ ID NO:1 that is N-terminal to at least three consecutive tripeptides selected from any combination of the following tripeptides Gly-Gly-Ala, Gly-Ala-Gly, Gly-Gly-Gly, Ala-Gly-Ala, or Ala-Gly-Gly, which are N-terminal to an amino acid sequence with at least 90% amino acid sequence identity to residues 328 to 641 of SEQ ID NO:1, wherein the recombinant protein lacks residues 65 to 89 of the wild-type EBNA-1 protein, wherein the recombinant protein binds an oriP of EBV with an affinity that is at least 10% that of the binding of the wild-type EBNA-1 protein, is noncytotoxic, and activates transcription at levels at least 5% that of the wild-type EBNA-1 protein from an extrachromosomal template having an oriP of EBV which is capable of binding the wild-type EBNA-1 protein.

21. The method of claim 19 wherein the DNA segment is on a second recombinant plasmid.

22. The method of claim 19 or 20 wherein the heterologous open reading frame encodes a therapeutic or prophylactic gene product.

23. The method of claim 19 or 20 wherein the heterologous open reading frame is operably linked to a promoter to form an expression cassette.

24. The method of claim 19 or 20 wherein the recombinant protein activates transcription from the plasmid at levels at least 10% that of the corresponding wild-type protein.

25. The method of claim 19 or 20 wherein the cell is a cultured or primary cell.

26. The method of claim 25 wherein the cell is a mammalian cell.

27. The method of claim 19 or 20 wherein a mammal is contacted with the recombinant plasmid.

28. A recombinant vector comprising:
a DNA segment which encodes a recombinant protein that is noncytotoxic relative to a wild-type EBNA-1 protein having SEQ ID NO:1, which recombinant protein has the following sequences: an amino acid sequence with at least 90% amino acid sequence identity to residue 1 to residue 40 of a wild-type EBNA-1 protein of EBV having SEQ ID NO:1 that is N-terminal to at least three consecutive tripeptides selected from any combination of the following tripeptides Gly-Gly-Ala, Gly-Ala-Gly, Gly-Gly-Gly, Ala-Gly-Ala, or Ala-Gly-Gly, which are N-terminal to an amino acid sequence with at least 90% amino acid sequence identity to residues 328 to 641 of SEQ ID NO:1, wherein the recombinant protein lacks residues 65 to 89 of the wild-type EBNA-1 protein, wherein the recombinant protein binds an oriP of EBV with an affinity that is at least 10% that of the wild-type EBNA-1 protein, and activates transcription at levels at least 5% that of the wild-type EBNA-1 protein from an extrachromosomal template having an oriP of EBV which is capable of binding the wild-type EBNA-1 protein;
the DNA sequence which binds the wild-type protein; and
a DNA fragment with a multiple cloning site sequence 3' to a promoter.

29. The vector of claim 28 further comprising a heterologous open reading frame inserted into a cloning site in the multiple cloning site sequence.

30. The recombinant vector of claim 28 which encodes a recombinant protein with at least 95% amino acid sequence identity to residues 1 to 40 and residues 328 to 641, and lacks residues about 65 to 89, of the wild-type EBNA-1 protein having SEQ ID NO:1.

31. The recombinant vector of claim 1 which encodes a recombinant protein having at least 90% amino acid sequence identity to residues 1 to 64 and residues 90 to 641 of SEQ ID NO:1.

32. The recombinant vector of claim 31 which encodes a recombinant protein having residues 1 to 64 and residues 90 to 641 of SEQ ID NO:1.

33. The method of claim 19 or 20 wherein the recombinant protein has at least 90% amino acid sequence identity to residues 1 to 64 and residues 90 to 641 of SEQ ID NO:1.

34. The method of claim 33 wherein the recombinant protein has residues 1 to 64 and residues 90 to 641 of SEQ ID NO:1.

35. The vector of claim 28 wherein the recombinant protein has at least 90% amino acid sequence identity to residues 1 to 64 and residues 90 to 641 of SEQ ID NO:1.

36. The vector of claim 35 wherein the recombinant protein has residues 1 to 64 and residues 90 to 641 of SEQ ID NO:1.

* * * * *

UNITED STATES PATENT AND TRADEMARK OFFICE
CERTIFICATE OF CORRECTION

PATENT NO.        : 7,465,580 B2
APPLICATION NO.   : 10/848976
DATED             : December 16, 2008
INVENTOR(S)       : Sugden et al.

It is certified that error appears in the above-identified patent and that said Letters Patent is hereby corrected as shown below:

On the title page, item (56), under "Other Publications", in column 2, line 7, below "1083-1090:" insert -- Bodescot, M., et al., "Clustered Alternative Splice Sites in Epstein-Barr Virus RNAs". Nucleic Acids Research, 15(14), (1987), 5887. --.

In column 52, lines 50-51, in Claim 14, delete "extracbromosomal" and insert -- extrachromosomal --, therefor.

In column 53, line 39, in Claim 20, delete "noncytotoxic." and insert -- noncytotoxic, --, therefor.

In column 54, line 44, in Claim 32, delete "lD" and insert -- ID --, therefor.

In column 54, line 47, in Claim 33, delete "lD" and insert -- ID --, therefor.

In column 54, line 49, in Claim 34, delete "lD" and insert -- ID --, therefor.

Signed and Sealed this

Twenty-third Day of June, 2009

JOHN DOLL
*Acting Director of the United States Patent and Trademark Office*